United States Patent
Huddleston et al.

(10) Patent No.: US 11,439,507 B2
(45) Date of Patent: Sep. 13, 2022

(54) TETHER ATTACHMENT ASSEMBLY FOR EPICARDIAL PADS AND DEVICES AND METHODS OF DELIVERY FOR SAME

(71) Applicant: Tendyne Holdings, Inc., St. Paul, MN (US)

(72) Inventors: Preston James Huddleston, Maplewood, MN (US); Zachary Vidlund, Robbinsdale, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 71 days.

(21) Appl. No.: 17/052,704

(22) PCT Filed: May 13, 2019

(86) PCT No.: PCT/US2019/031984
§ 371 (c)(1),
(2) Date: Nov. 3, 2020

(87) PCT Pub. No.: WO2019/231653
PCT Pub. Date: Dec. 5, 2019

(65) Prior Publication Data
US 2021/0236287 A1 Aug. 5, 2021

Related U.S. Application Data

(60) Provisional application No. 62/679,094, filed on Jun. 1, 2018.

(51) Int. Cl.
*A61F 2/24* (2006.01)

(52) U.S. Cl.
CPC .......... *A61F 2/2481* (2013.01); *A61F 2/2412* (2013.01); *A61F 2/2436* (2013.01)

(58) Field of Classification Search
CPC .................. A61F 2/2418; A61F 2/2457; A61F 2220/0075; A61F 2/2439; A61F 2/24;
(Continued)

(56) References Cited

U.S. PATENT DOCUMENTS

| 7,736,388 B2 * | 6/2010 | Goldfarb | ............ A61B 18/1492 606/139 |
| 2004/0138521 A1 * | 7/2004 | Grabek | ................. A61F 2/2481 600/37 |

(Continued)

FOREIGN PATENT DOCUMENTS

| EP | 2111800 A1 | 10/2009 |
| WO | 2015017689 A1 | 2/2015 |

(Continued)

OTHER PUBLICATIONS

International Search Report including the Written Opinion for Application No. PCT/US2019/031984 dated Sep. 17, 2019, pp. 1-16.

*Primary Examiner* — Seema Mathew
(74) *Attorney, Agent, or Firm* — Wei & Sleman LLP

(57) ABSTRACT

Apparatus and methods are described herein for use in the delivery of a prosthetic mitral valve. In some embodiments, an apparatus includes a tether fixer assembly configured to engage an outside surface of a heart to secure a prosthetic heart valve in position within the heart. The fixer assembly defines a lumen configured to receive therethrough a tether extending from the prosthetic valve and a movable portion. The fixer assembly is movable between a first configuration, in which the movable portion is disengaged with the tether, and a second configuration in which the movable portion is engaged with the tether. The fixer assembly can be disposed against an epicardial pad positioned on the outside surface of the heart when in the second configuration to secure the (Continued)

prosthetic valve, the epicardial pad and tether in a desired position within the heart.

10 Claims, 14 Drawing Sheets

(58) Field of Classification Search
CPC .... A61F 2/2481; A61F 2/2478; A61F 2/2442; A61F 2/2487; A61F 2002/249; A61F 2/2454
See application file for complete search history.

(56) References Cited

U.S. PATENT DOCUMENTS

| | | | | |
|---|---|---|---|---|
| 2004/0243170 A1* | 12/2004 | Suresh | ................. | A61F 2/2487 606/198 |
| 2004/0249408 A1* | 12/2004 | Murphy | ................. | A61F 2/2487 606/198 |
| 2005/0102015 A1* | 5/2005 | Lau | ................. | A61F 2/2481 607/129 |
| 2006/0025800 A1* | 2/2006 | Suresh | ................. | A61F 2/2487 606/198 |
| 2009/0177028 A1* | 7/2009 | White | ................. | A61M 60/268 600/37 |
| 2011/0021864 A1* | 1/2011 | Criscione | ................. | A61M 60/148 600/16 |
| 2011/0029071 A1 | 2/2011 | Zlotnick et al. | | |
| 2014/0324161 A1* | 10/2014 | Tegels | ................. | A61F 2/2439 623/2.11 |
| 2016/0143736 A1* | 5/2016 | Vidlund | ................. | A61B 17/0057 623/2.4 |
| 2017/0079790 A1 | 3/2017 | Vidlund et al. | | |
| 2017/0312077 A1 | 11/2017 | Vidlund et al. | | |
| 2018/0078370 A1* | 3/2018 | Kovalsky | ................. | A61F 2/2433 |

FOREIGN PATENT DOCUMENTS

| | | |
|---|---|---|
| WO | 2015120122 A2 | 8/2015 |
| WO | 2016126942 A2 | 8/2016 |

* cited by examiner

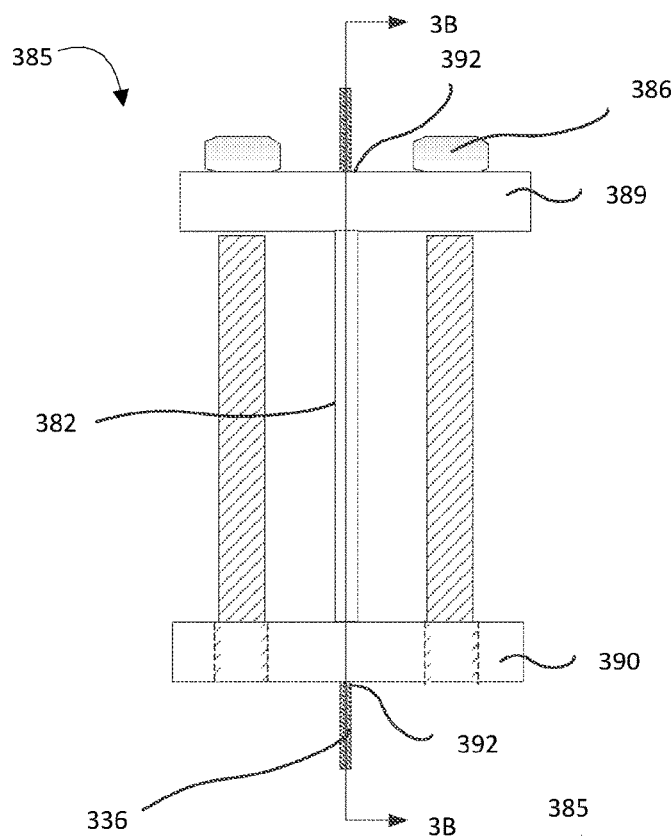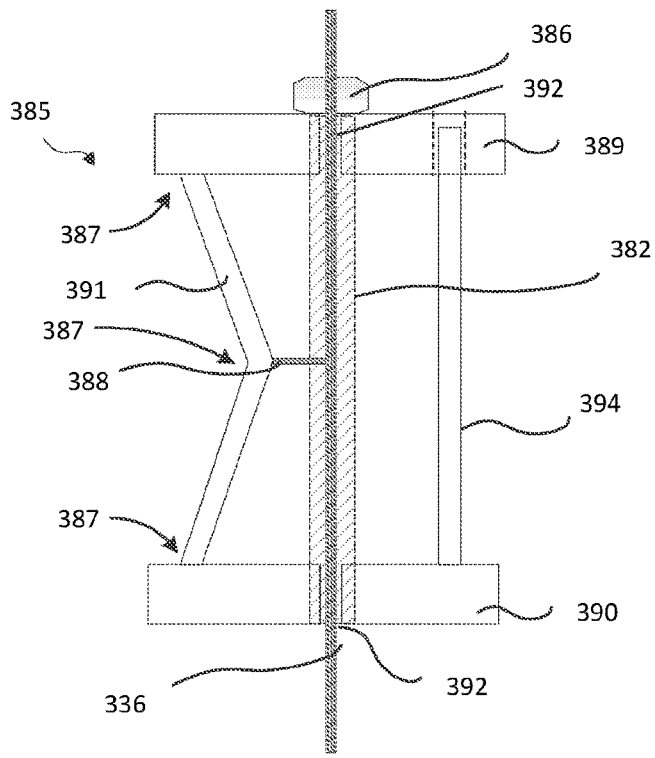
FIG. 3A
FIG. 3B

TETHER ATTACHMENT ASSEMBLY FOR EPICARDIAL PADS AND DEVICES AND METHODS OF DELIVERY FOR SAME

CROSS-REFERENCE TO RELATED APPLICATIONS

The present application is a national phase entry under 35 U.S.C. § 371 of International Application No. PCT/US2019/031984 filed May 13, 2019, published in English, which claims the benefit of the filing date of U.S. Provisional Patent Application No. 62/679,094, filed Jun. 1, 2018, entitled Tether Attachment Assembly For Epicardial Pads And Devices And Methods For Delivery Of Same, the entire disclosures of which are hereby incorporated herein by reference in their entireties.

BACKGROUND OF THE DISCLOSURE

Embodiments are described herein that relate to devices and methods for delivery, deployment, and securement of prosthetic valves and epicardial pads.

Some known devices for anchoring a medical device, such as, for example, a prosthetic heart valve (e.g. mitral valve) can include securing one or more tethers extending from the medical device to body tissue. For example, one or more tethers can extend from a prosthetic heart valve through an opening in the ventricular wall of the heart. Some known methods of anchoring or securing the tethers can include the use of staples or other fasteners that engage or pierce tissue near the puncture site. Such devices can have relatively large profiles and be difficult to easily deliver percutaneously to the desired anchoring site. Some known methods of securing a prosthetic heart valve can include suturing the tethers extending from the valve to body tissue, or tying the suture ends. Such devices and methods can be difficult to maneuver to secure the tether(s) with a desired tension, Further, when an opening is made directly into the ventricular wall or apex of a heart, such as when a prosthetic valve is percutaneously delivered and deployed, in addition to securing the prosthetic valve in a proper position, the efficacy of sealing the puncture site is critical to the life of the patient since hemodynamic losses from a cardiac puncture can cause shock and death within minutes. In addition, the outward pressure that the puncture site is subjected to when it is located in the heart muscle itself is much higher than puncture sites that are distal to the heart.

Accordingly, improved devices and methods for securing a prosthetic heart valve and for engaging and closing tissue, e.g., to close a cardiac puncture site, would be considered useful to solve these and other problems known in the art.

BRIEF SUMMARY

Devices and methods for use in the delivery and deployment of a prosthetic valve and an epicardial pad are described herein. As described herein, in some embodiments, a method includes delivering and deploying a fixer assembly to secure an expandable epicardial pad. The fixer or fixer assembly can be used to hold or otherwise affix an epicardial pad disposed at or near an apex of a heart. In some embodiments, after a prosthetic mitral valve has been deployed within the heart via a transfemoral, transjugular or other suitable delivery approach, a tether attached to the prosthetic valve can be used to secure the prosthetic valve. The tether can extend through a minimally invasive opening at the apex of the heart, and the tether can be secured using an epicardial pad against the apex of the heart. A fixer assembly can be used to secure the tether to the epicardial pad and hold the epicardial pad against the apex of the heart, such that the epicardial pad, the tether and the attached prosthetic valve may be held in a desired position. In some embodiments, the epicardial pad can be an expandable epicardial pad, with a fixer assembly used to secure the expanded epicardial pad.

BRIEF DESCRIPTION OF THE DRAWINGS

FIG. 3A is a schematic illustration of a side view of a fixer assembly, in a first configuration, according to an embodiment.

FIG. 3B is an illustration of a cross-sectional view of the fixer shown in FIG. 3A, taken along the line 3B-3B.

DETAILED DESCRIPTION

Figure 1:
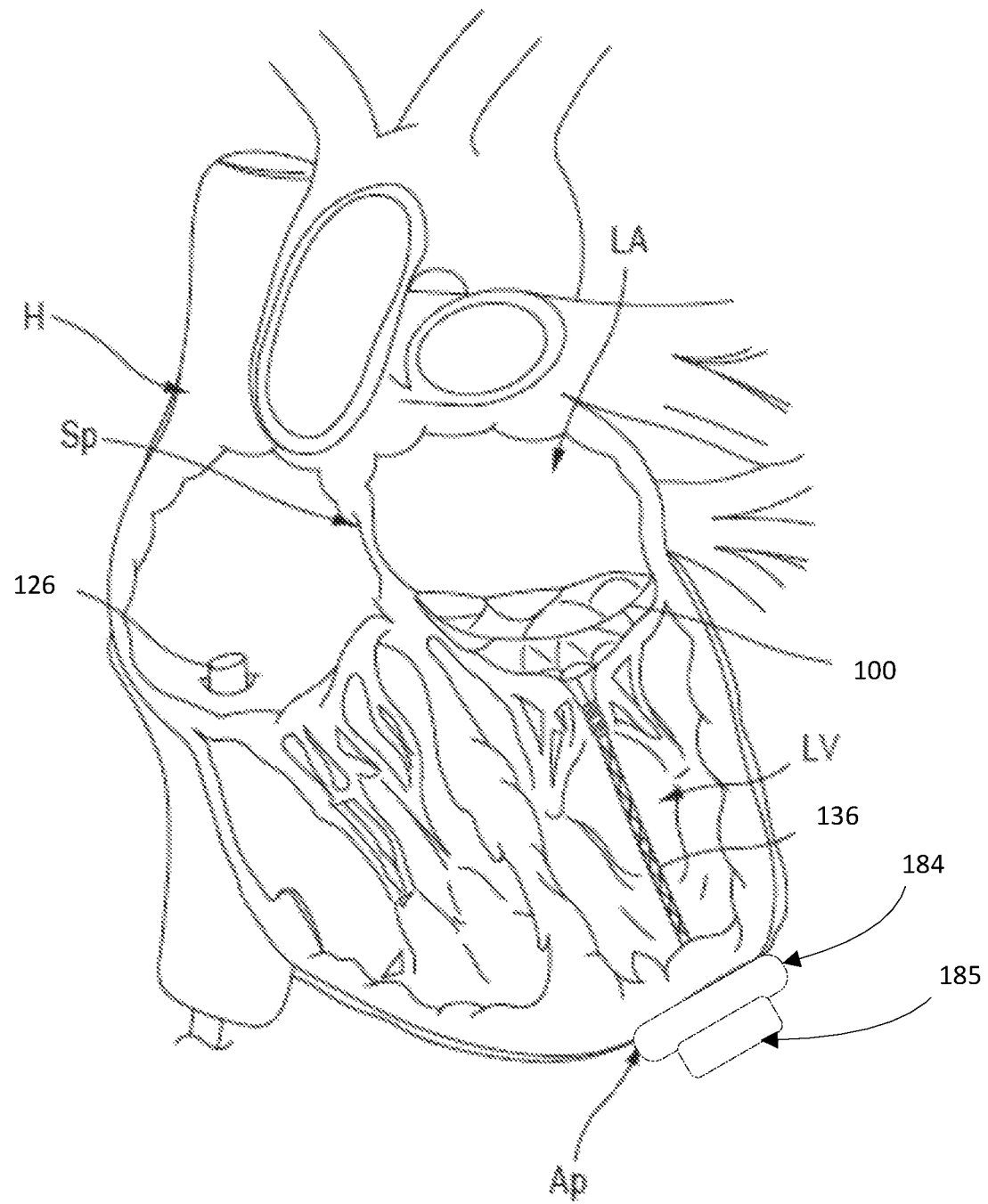
FIG. 1 is a cross-sectional illustration of a portion of a heart with a prosthetic mitral valve implanted therein, secured by an epicardial pad and a fixer assembly.

Devices and methods for use in the delivery and deployment of prosthetic mitral valves and epicardial pads are described herein. As described herein, in some embodiments, a method includes delivering and deploying an epicardial pad and a fixer assembly to hold a prosthetic valve in place against an apex of a heart. In some embodiments, the epicardial pad can be expandable upon deployment adjacent to or near the apex region of a heart, and the expanded epicardial pad can be held in place by the fixer assembly. In some embodiments, after a prosthetic valve has been deployed within the heart via a transcatheter or other suitable delivery approach, a tether attached to the prosthetic valve can extend outside the apex of the heart. The epicardial pad and a fixer assembly can be deployed through a minimally invasive opening at the apex region of the heart to secure the tether and the prosthetic valve in a desired position.

The prosthetic valve can be delivered to be placed within a patient's heart using a variety of different delivery approaches for delivering a prosthetic heart valve (e.g., prosthetic mitral valve). For example, the prosthetic valves described herein can be delivered using a transfemoral delivery approach as described in International Application No. PCT/US15/14572 (the '572 PCT application) the disclosure of which is incorporated herein by reference in its entirety, or via a transatrial approach or a transjugular approach, such as described in U.S. Patent Application Publication No. 2017/0079790 the disclosure of which is incorporated herein by reference in its entirety. The prosthetic valves described herein can also be delivered apically if desired.

In some embodiments, an apparatus includes an epicardial pad configured to engage an outside surface of a heart to secure a prosthetic heart valve in position within the heart. The prosthetic heart valve has a tether extending therefrom and outside the heart when the prosthetic heart valve is disposed within the heart. The epicardial pad defines a lumen configured to receive the tether therethrough. The epicardial pad is movable between a first configuration in which the epicardial pad has a first outer perimeter and is configured to be disposed within a lumen of a delivery sheath and a second configuration in which the epicardial pad has a second outer perimeter greater than the first outer perimeter. The epicardial pad can be disposed against the outside surface of the heart when in the second configuration to secure the prosthetic valve and tether in a desired position within the heart.

In some embodiments, an apparatus includes a fixer assembly to hold the epicardial pad engaged against the outside surface of an apex of a heart, securing a prosthetic valve in position. The prosthetic heart valve has a tether extending therefrom and outside the heart when the prosthetic heart valve is disposed within the heart, and the tether extends further through the epicardial pad. The fixer assembly defines a lumen configured to receive the tether therethrough. The fixer assembly is movable between a first configuration in which the fixer device can slide along the tether and a second configuration in which the fixer device is engaged with the tether securing the relative position of the fixer assembly and the epicardial pad with respect to the tether.

In some embodiments, an expandable epicardial pad and the fixer assembly can be delivered to the apex region of a heart using a delivery device as described herein. The delivery device can include a handle assembly having one or more control actuators and engagement devices to engage with the epicardial pad and/or fixer assembly. The delivery device can also have a delivery sheath that defines one or more lumens in which the epicardial pad and fixer assembly can be disposed during delivery to the heart. For example, the epicardial pad can be in a first configuration in which the outer diameter of the epicardial pad is sized to be received within the lumen. The fixer assembly can also be sized to be disposed within the lumen of the delivery device.

In some embodiments, a delivery device can include a first lumen and a dilator device that defines a second lumen and is movably disposed within the first lumen of the delivery sheath. Such a delivery device is described in U.S. Patent Application Publication No. 2017/0312077 ("the '077 publication"), the disclosure of which is incorporated herein by reference in its entirety. The dilator device includes an elongate member and an expandable member disposed at a distal end of the elongate member. The expandable member has a collapsed configuration and an expanded configuration. The dilator device is in the collapsed configuration when disposed within the first lumen. An epicardial pad having a collapsed configuration and an expanded configuration is configured to be disposed within the second lumen when in the collapsed configuration. The epicardial pad is configured to be disposed against an outside surface of a heart when in the expanded configuration. The dilator member of the dilator device is configured to dilate tissue associated with the outside surface of the heart when moved from its collapsed configuration to its expanded configuration such that a space is formed in which the epicardial pad can be disposed.

In some embodiments, the delivery sheath also removably houses the fixer assembly that is held in place during deployment via the engagement devices in the delivery device. The fixer assembly is configured to be in the first configuration until disposed against the expanded epicardial pad in the desired position, and then configured to transition to a second configuration of being engaged with the tether, through the operation of one or more actuators in the delivery device.

In some embodiments, a method includes disposing a distal end portion of a delivery sheath outside a surface of a heart near an apex of the heart. The delivery sheath has an epicardial pad disposed within a lumen of the delivery sheath. The epicardial pad has a collapsed configuration when disposed within the lumen of the delivery sheath and an expanded configuration. The epicardial pad defines an opening and has a tether extending through the opening. The tether is coupled to a prosthetic heart valve implanted within the heart. In some embodiments, the epicardial pad can include an attachment device (e.g. a pin) for securing the epicardial pad to the tether through a suitable method (e.g., piercing of the tether with the pin). In some other embodiments, particularly when the epicardial pad may be configured to be delivered in a collapsed configuration through a minimally invasive opening, the epicardial pad may not include any attachment device. Instead, the delivery sheath or delivery device that delivers and deploys the epicardial pad can include the delivery of a tether fixer assembly that is sized and configured to be delivered through a minimally invasive opening. The fixer assembly can include one or more attachment devices (e.g., pins, clamps, clips, vises, etc.) that can be suitably used to secure the tether fixer assembly as well as the epicardial pad in the desired position, for example against the apex of a heart. At deployment, the epicardial pad and the fixer assembly are disposed outside a distal end of the delivery sheath and outside the surface of the heart near the apex of the heart. The epicardial pad is secured in an expanded configuration to the outside surface of the heart by the fixer assembly, to secure the prosthetic heart valve and the tether in a desired position.

In some embodiments, a method includes disposing a distal end portion of a delivery sheath outside a surface of a heart near an apex of the heart. The delivery sheath has, in addition to the epicardial pad, a fixer assembly disposed within a lumen of the delivery sheath. The epicardial pad is in a collapsed configuration within the delivery sheath. The epicardial pad and the tether fixer assembly each define a lumen or an opening that can receive the tether therethrough such that the tether extends out a proximal end of the delivery sheath. The tether fixer assembly has a first configuration when disposed within the lumen of the delivery sheath, in which it is disengaged with the tether and can be moved relative to the tether along the longitudinal axis defined by the tether extending through the lumen or opening. The tether fixer assembly has a second configuration in which it is secured onto the tether, fixing its position along the length of the tether. The tether fixer assembly can include attachment devices and/or actuators that can be used to transition the fixer assembly from the first configuration to the second configuration upon deployment as described in more detail below.

With the distal end of the delivery device disposed outside the heart near the apex, the epicardial pad and the fixer assembly can be moved (e.g., along the tether) outside the distal end of the delivery sheath and to a location at or near the apex of the heart. More specifically, the epicardial pad can be moved distally (along the tether) into contact with the outer surface of the heart and can be actuated to be moved to an expanded configuration. The tether fixer can be moved distally into contact with a proximal side of the epicardial pad and can be actuated to engage the tether such that the fixer assembly can no longer move relative to the tether. In other words, the tether is secured to the fixer assembly. With the epicardial pad and fixer assembly secured to the tether, the delivery device can be removed and the tether can be cut at a proximal side of the fixer assembly.

FIG. 1 is a cross-sectional illustration of a portion of a heart H showing the left ventricle LV and left atrium LA of the heart having a transcatheter prosthetic mitral valve 100 deployed therein and an epicardial anchor device 184 securing the prosthetic mitral valve 100 to the apex region Ap of the heart. Such a prosthetic mitral valve 100 can be delivered to the heart, for example, via a transfemoral approach through the septum Sp using a delivery device 126 (shown being removed after delivery). FIG. 1 illustrates the prosthetic mitral valve 100 seated into the native valve annulus and held there using an atrial cuff of the prosthetic mitral valve 100, the radial tension from the native leaflets, and a ventricular tether 136. The tether 136 is secured to the prosthetic mitral valve 100, to the epicardial anchor device 184 and to a tether fixer device 185 (also referred to herein as "tether fixer" or "fixer"). The epicardial anchor device 184 can be, for example, an expandable epicardial pad and the fixer device 185 can be a fixer assembly, as described in further details herein. The apparatus and methods described herein can be used in conjunction with various different types and embodiments of an epicardial anchor device, such as those described in pending International Patent Application No. PCT/US14/49218 entitled "Epicardial Anchor Devices and Methods," ("PCT application '49218") the disclosure of which is incorporated herein by reference in its entirety, or those described in the '077 publication incorporated by reference above.

Figure 2:
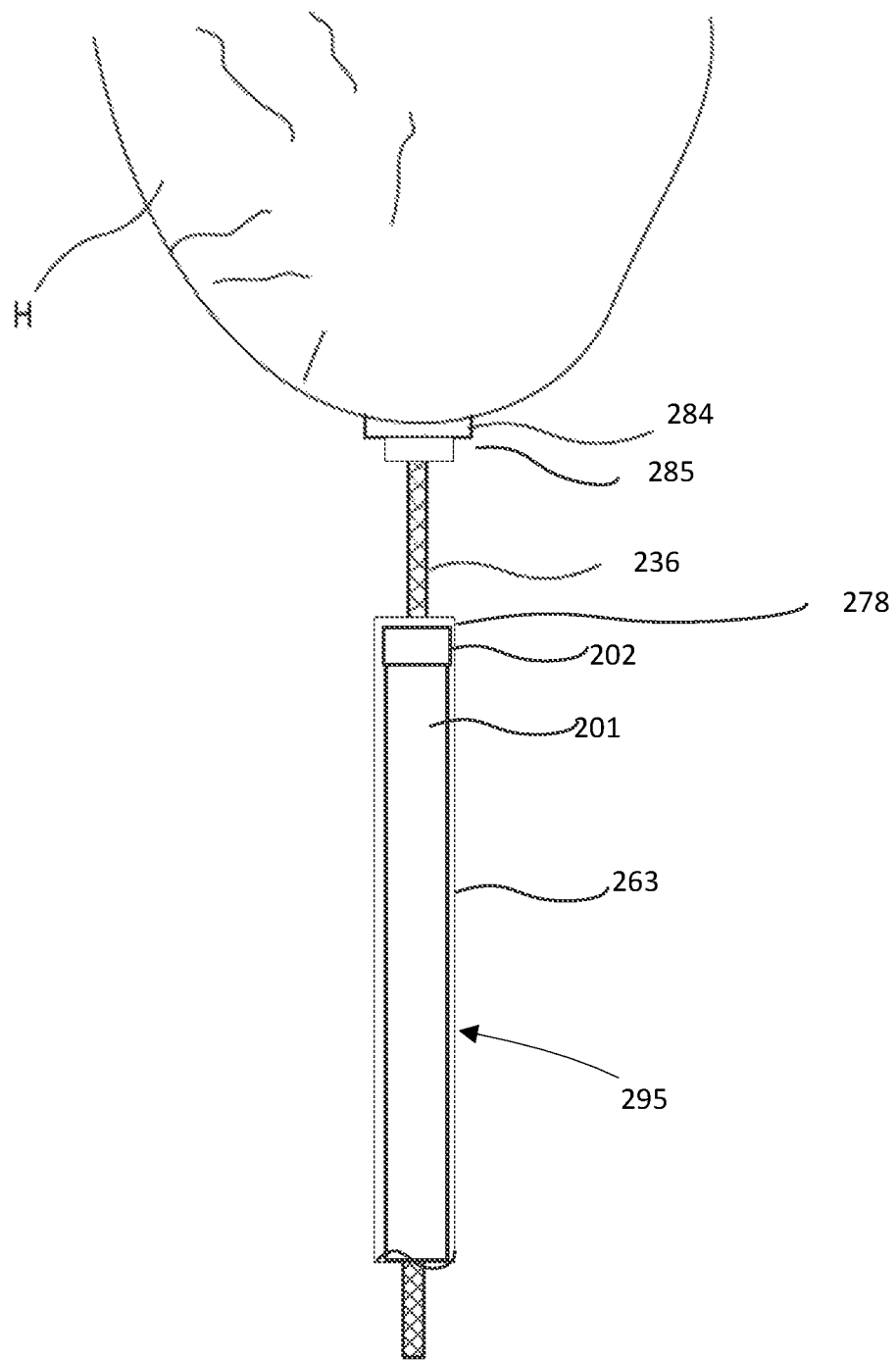
FIG. 2 is a schematic illustration of a portion of a heart with an epicardial pad and fixer assembly disposed thereon, and a delivery device to deliver the fixer assembly, according to an embodiment.

FIG. 2 illustrates an embodiment of an epicardial pad device 284 and an embodiment of a tether fixer assembly 285 that can be used to secure a tether 236 attached to a prosthetic mitral valve (not shown) to a heart H, for example, at the apex of the heart. The tether fixer assembly 285 (also referred to herein as "fixer assembly" or "fixer") can be used to secure the epicardial pad device 284 (also referred to herein as "epicardial pad" or "apical pad" or "pad") against the apex of the heart, for example, during a procedure to deliver a prosthetic heart valve as described herein. The tether fixer assembly 285 includes a lumen or an opening to allow the tether 236 of a prosthetic heart valve to extend through the opening. The tether fixer assembly 285 includes one or more tether attachment or tether fastening portions or devices (not shown in FIG. 2) such as clamps, pins, clips, vises, collets, hooks, etc. that can be used to secure the tether fixer assembly 285 to the tether 236. More specifically, the tether fixer assembly 285 can be moved from a first configuration in which the tether fastening devices/portions are not engaged with the tether 236 and the fixer assembly 285 can move relative to the tether 236, and a second configuration in which the tether fastening portions of the fixer assembly 285 can engage the tether 236 and be secured thereto, thus preventing the tether fixer 285 from moving relative to the tether 236. The tether fixer assembly 285 also includes one or more actuators or engagement portions that can be actuated by an actuator of a delivery device to operably transition the tether fixer assembly 285 from the first configuration to the second configuration as described in more detail below with reference to specific embodiments. The epicardial pad 284 and the tether fixer assembly 285 can each be formed with one or more of any suitable material. For example, a suitable polymer or metal material such as, for example, PEEK plastic, or stainless steel such as, for example, MP35N stainless steel. In some embodiments, the epicardial pad 284 can be, for example, an expandable epicardial pad as described in PCT application '49218, incorporated by reference above.

In some embodiments, as shown in FIG. 2, the epicardial pad 284 and the fixer assembly 285 can be delivered to the exterior of the heart via a small incision and a delivery device 295 with a small diameter delivery catheter or sheath 263. In some embodiments, the delivery catheter or delivery sheath 263 can have a diameter, for example, in the range of 3-5 mm. Thus, the fixer assembly 285 can be sized such that it can be delivered within the small diameter of the delivery sheath 263. As described above, the epicardial pad 284 can be expandable such that it can be collapsed for delivery within the delivery sheath 263 and then expanded at the site of the incision in the heart. The delivery device 295 can have an actuation device 201 (shown schematically in FIG. 2) that can be movably disposed within the delivery sheath 263 and include an engagement portion 202 that can be releasably engaged with the fixer assembly 285 during delivery. The actuation device 201 can be used to manipulate or actuate the fixer assembly 285 to transition the fixer assembly 285 between the first configuration and the second configuration. The illustration in FIG. 2 shows the fixer assembly 285 after being deployed and placed abutting the epicardial pad 284, securing the epicardial pad against the apex of the heart, securing the prosthetic valve in the desired position.

In use, after a prosthetic mitral valve has been deployed within the heart H, for example, via a transfemoral delivery approach as described in the '572 PCT application incorporated by reference above, the tether 236 attached to the prosthetic valve (not shown) can extend outside the apex of the heart H. The tether 236 can be received through the respective openings of the epicardial pad 284 and the fixer assembly 285, which in turn can be placed within a lumen of the delivery sheath 263 with the tether 236 extending proximally from the delivery sheath 263. The actuation device 201 of the delivery device 295 can engage the tether fixer assembly 285 to hold the fixer assembly 285 during delivery. Similarly, the delivery device 295 can include features to engage with and hold the epicardial pad 284. The delivery sheath 263 housing the epicardial pad 284 and the fixer assembly 285 can be inserted through a small incision in the skin of the patient and a distal end of the delivery sheath can be disposed at a desired location near the apex of the heart. The epicardial pad 284 (e.g., an expandable epicardial pad) can be moved outside of the delivery sheath 263 and then expanded as shown in FIG. 2.

The fixer assembly 285 can also be moved outside the delivery sheath 263 either simultaneously or sequentially with the epicardial pad 284. For example, to move the epicardial pad 284 and/or the tether fixer assembly 285 outside of the lumen of the delivery sheath 263, the delivery sheath 263 can be retracted proximally, such that the epicardial pad 284 and the tether fixer assembly 285 are disposed outside a distal end 278 of the delivery device 295. Alternatively, the epicardial pad 284 and the tether fixer assembly 285 can be moved or pushed distally out of the lumen of the delivery sheath 263 using a pushing mechanism, for example, a push rod (not shown) that can be operated within the lumen of the delivery sheath 263. In some embodiments, the delivery sheath 263 can have two or more inner lumens for the release and positioning of the epicardial pad 284 and for the positioning, actuation and release of the tether fixer assembly 285, as described below. In some embodiments, separate devices can be used to deliver the epicardial pad 284 and the fixer assembly 285.

As described above, after moving the epicardial pad 284 outside of the delivery sheath 263, the epicardial pad 284 can be expanded to a larger size. In some embodiments, the fixer assembly 285 may also have a larger deployed size. In some embodiments, the epicardial pad 284 can be formed with a shape-memory material such that upon being released from the lumen of the delivery sheath 263, the epicardial pad 284 can assume an expanded form when moved outside the distal end of the delivery sheath 263. In some embodiments, the epicardial pad 284 can be actuated to move from a collapsed configuration for delivery and an expanded configuration for use.

After deploying the epicardial pad 284 out of the delivery sheath 263, the epicardial pad 284 can be moved distally into contact with the heart, with the tether extending through an opening or lumen in the epicardial pad 284, where the pad 284 can be pushed against the apex of the heart, as shown in FIG. 2. The tether fixer assembly 285 can be moved distally against the epicardial pad 284, with the tether 236 extending through the opening in the tether fixer assembly 285, pushing the epicardial pad 284 against the apex of the heart. The epicardial pad 284 and the fixer assembly 285 can be positioned against the heart simultaneously or sequentially. The tether fixer assembly 285 and the epicardial pad 284 can be moved along the tether 236 and pushed against the apex of the heart to a suitable degree that ensures desired positioning of the epicardial pad with respect to the heart.

In some embodiments, the epicardial pad 284, if expandable, can be fully expanded during or after final positioning of the epicardial pad 284 and the fixer assembly 285, using any suitable expansion mechanism. As described above, in some embodiments, the fixer assembly 285 can also be expandable, in which case, the fixer assembly 285 can also be fully expanded during or after positioning of the epicardial pad and the fixer assembly 285 along the tether 236, using any suitable inflation or expansion mechanism. For example, the delivery device 295 can include an inflation mechanism and/or a separate device can be used inflate and/or deflate the expandable epicardial pad 284 or the expandable tether fixer assembly 285, to position and/or remove or reposition them, as needed, for example, during a process of repositioning a prosthetic valve within the heart.

In some embodiments, the fixer assembly 285 and/or the epicardial pad 284 can have a connecting portion(s) (e.g., screw head and tapped hole, clamps that couple, etc.) that allow releasable coupling between them. In other words, the fixer assembly 285 and the epicardial pad 284 can be configured to be matingly connected with each other during deployment. The delivery device 295 can include one or more actuation portions that actuate the fixer assembly 285 and/or the epicardial pad 284 such that they are matingly coupled during delivery of the fixer assembly 285. Upon positioning of the epicardial pad 284 and/or the tether fixer assembly 285, in some embodiments, if the epicardial pad 284 and/or the tether fixer assembly 285 are expandable, they can be fully deflated and can be filled with an adhesive or a cement material to add strength and rigidity.

With the tether fixer assembly 285 and the epicardial pad 284 disposed at a desired position along the tether 236 (and against the heart), the tether fixer assembly 285 can be actuated by the actuation device 201 to actuate the one or more attachment or fastening portions (not shown in FIG. 2) in the tether fixer assembly 285. The one or more attachment or fastening portions can engage (e.g., pierce, clamp, etc.) with the tether 236, securing the position of the tether fixer assembly 285 relative to the tether 236. With the epicardial pad 284 and fixer assembly 285 secured to the tether 236, the delivery device 295 can be removed and the tether 236 can be cut at a proximal side of the fixer assembly 285.

In some embodiments, prior to deployment of the epicardial pad 284 and the fixer assembly 285, as described herein, an expandable tissue dilator device (not shown) as described in the '077 publication incorporated by reference above, can be used to dilate tissue or otherwise create space suitable for delivery and/or deployment of the epicardial pad 284 and the tether fixer assembly 285. The epicardial pad 284 can be, for example, the same as or similar to any epicardial pad device described herein or in the '077 publication, or in International PCT Application No. PCT/US2014/0049218 (the '218 PCT Application), and can be used in the same or similar manner as described for previous embodiments herein or in the '218 PCT Application to secure a tether attached to a prosthetic mitral valve to the heart, for example, at the apex of the heart.

In some embodiments of a fixer assembly described herein, the actuators of the fixer assembly can include one or more rotary turning devices, such as, for example, screws that are coupled to collapsible pins, and rotary actuation results in the collapse of the pins which pierce and fix the tether. FIGS. 3A and 3B illustrate a tether fixer assembly 385, according to one such embodiment. The fixer assembly 385 can be used in a similar manner as the fixer assembly 185 and 285 described above. For example, the fixer assembly 385 can be delivered to an apex of a heart using a delivery device as described above, and used to secure a tether to an epicardial pad through one or more attachment or fastening devices as described above.

For example, the fixer assembly 385 illustrated in FIGS. 3A and 3B includes a top or proximal engagement portion 389 and a bottom or distal portion 390, each coupled to an elongate member 382. The elongate member 382 defines an internal lumen 392 through which a tether 336 that is coupled to a prosthetic valve deployed within a heart (not shown) can be received as shown in FIGS. 3A and 3B. The fixer 385 also includes one or more posts 391 and 394, and one or more actuation portions 386.

The top engagement portion 389 is configured to engage with an engagement portion of a delivery device (e.g. the engagement portion 202 of the delivery device 295 illustrated schematically in FIG. 2). For example, in some embodiments, the top engagement portion 389 can be held by the engagement portion of the delivery device, during delivery and/or deployment of the fixer assembly 385, through a suitable clamping, pinning or gripping mechanism. The engagement between the delivery device and the fixer 385 can be used to control the position and state of the fixer 385 during delivery and deployment, such as during actuation.

With the tether 336 extending through the lumen 392, the fixer assembly 385 can be delivered using a delivery device (not shown in FIGS. 3A and 3B) coupled via the engagement portion 389, as described above. More specifically, the fixer assembly 385 can be moved or slid along the tether 336 into a desired position near an epicardial pad (not shown in FIGS. 3A and 3B) as described above for previous embodiments. The bottom portion 390 of the tether fixer assembly 385 can be placed against the epicardial pad, and one or more actuation portions 386 can be actuated to secure the fixer assembly 385 to the tether 336 as described in more detail below.

The engagement of the delivery device to the fixer 385 can be configured to minimize undesired relative movement of the fixer 385 along the longitudinal or circular axes of the tether 336. In some embodiments, the top engagement portion 389 of the fixer 385 and/or the engagement portion of the delivery device can include specialized structures (e.g., grooves, notches, furrows, etc. with corresponding ridges, pegs, pins, etc.) that matingly connect to each other in a releasably coupled manner. In some embodiments, the engagement can be through radial pressure of the delivery sheath around the top engagement portion 389 in the form of a circular plate of a suitable thickness. In yet other embodiments, the engagement can be through specialized structures such as grooves, notches, in for example, the top engagement portion 389 of the fixer 385, with corresponding pegs or pins in the engagement portion of the delivery device, that are held in engagement by the radial pressure of the delivery sheath.

The bottom portion 390 of the fixer 385 can be configured to be placed against an epicardial pad or the apex of a heart. In some embodiments of the fixer 385, when used to fix the position of an epicardial pad (not shown), the bottom portion 390 can be configured to couple with one or more portions of the epicardial pad in a releasable fashion. For example, in some embodiments, the bottom portion 390 can be threaded in its outer perimeter to couple with a tapped receiving portion of a compatible epicardial pad such that the fixer 385 can be screwed onto the compatible epicardial pad.

In this embodiment, the actuation portions 386 (also referred to herein as "actuator members" or "actuators") are in the form of cap screws or bolts with suitable screw heads and a suitable length with threading. The screws 386 are configured to pass through the top engagement portion 389 via throughholes and be screwed into the bottom portion 390, via tapped holes. The post 391 includes hinged portions 387 and a fastening device 388. The fastening device 388, which in this embodiment is in the form of a pin, is mounted on the hinged support structure 391 pointed radially toward the tether 336 extending through the lumen 392. The hinged post 391 can be, for example, a two-part bar with a hinge 387 located in the middle and hinges 387 at points of contact with the top portion 389 and the bottom portion 390. The fixer 385 is configured such that, in operation, when the screws 386 are advanced through the tapped holes in the bottom portion 390, the top portion 389 is moved toward the bottom portion 390, which in turn applies a force to the post 391 and causes the post 391 to fold at the hinges 387. This in turn drives the pin 388 through an opening in the elongate member 382 such that it pierces the tether 336. In some embodiments, the post 394 can be in the path of the driven pin 388 (e.g., can be positioned close to the elongate member 382) and in such an embodiment, the post 394 can include one or more openings or adaptations (not shown) to accommodate or receive the pin 388 after it passes through the tether 336. Although in this embodiment actuation portions 386 are implemented as threaded screws, other suitable mechanisms may be used to move the top portion 389 and bottom portion 390 towards each other.

Thus, in use, the actuation of the fixer 385 transitions the fixer assembly 385 from a first configuration of being disengaged with the tether 336, to a second configuration of being engaged with the tether 336.

Figure 4A:
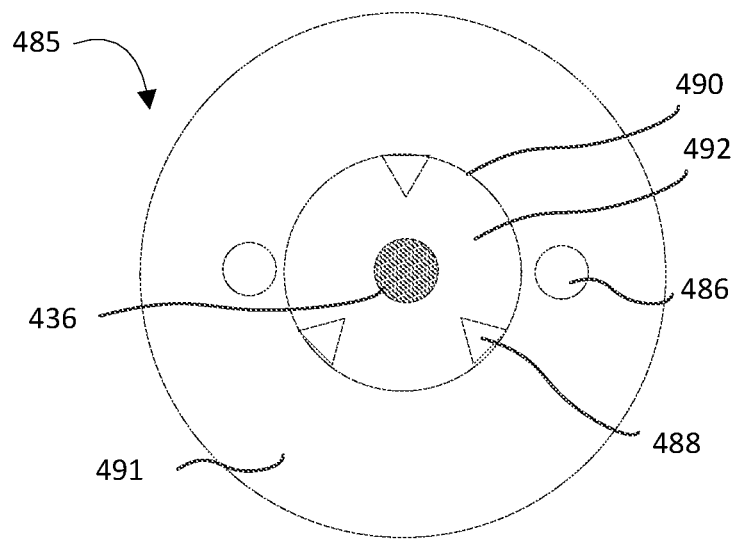
FIGS. 4A and 4B are schematic illustrations of a top view of a fixer assembly, in a first configuration and a second configuration, respectively, according to an embodiment.
Figure 4B:
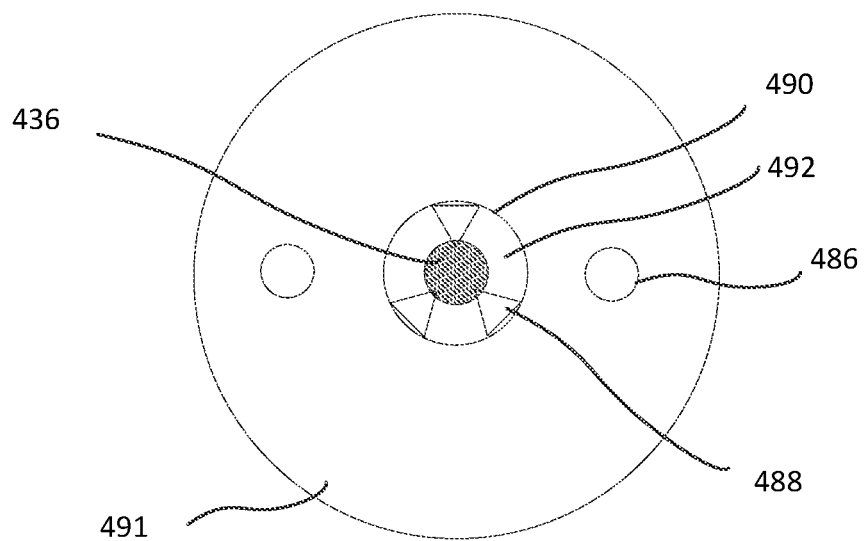

In another embodiment, a tether fixer assembly can include an expandable member with actuators to aid in controlled expansion of the expandable member by inflation of fluid or gas or other suitable material. The expandable member can be coupled to tether attachment devices such as collets or clamps or pins that upon expansion of the expandable member are driven into the tether to fasten the fixer relative to the tether. FIGS. 4A and 4B illustrate a fixer assembly 485 that includes an expandable member, according to an embodiment.

The fixer 485 can be used in a similar manner as the fixer assemblies described above to secure a tether to an epicardial pad. In this embodiment, the fixer assembly 485 can include an expandable portion 491 that defines an opening 492 through which a tether 436 can extend. The expandable portion 491 includes a proximal portion 489 and a distal portion (not shown). The distal portion can be configured to engage with the epicardial pad. The fixer 485 can have one or more tether attachment or tether fastening devices 488 (e.g., pins) mounted onto an inner surface of the expandable portion 491 within the opening 492, as shown in FIGS. 4A and 4B. The expandable portion 491 can include one or more ports 486 that can be used to couple the expandable portion 491 to a source of inflation medium to inflate the expandable portion 491 and move it between an unexpanded configuration and an expanded configuration.

More specifically, the expandable member 491 can be configured to have a fixed outer diameter when inflated and not inflated, but the diameter of the opening 492 or inner diameter of the expandable member 491 can be changed depending on the state of inflation or deflation of the expandable member 491. The fastening devices 488 (e.g., pins) can be pointed inward within the opening 492 and include sharp or piercing tips that can be used to pierce a tether 436 extending through the opening 492.

In use, the fixer 485 can be delivered to a desired location near an apex of a heart at the same time or after delivering an epicardial pad, as described above for previous embodiments. With the tether fixer 485 and/or the epicardial pad (not shown) in the desired position and the tether 436 extending through opening 492, the expandable portion 491 can be inflated using a suitable inflation mechanism through, for example, the delivery device. For example, the inflation ports 486 can be ports that allow pumping saline into the expandable portion 491 through the delivery device. In some embodiments, the ports 486 can also allow inflating the expandable balloon portion 491 with saline followed by pumping a hardening agent that is configured to aid in the expandable portion 491 retaining the inflated form. Upon inflation, the inner diameter (i.e., opening 492) of the expandable portion 491 reduces in size resulting in the tether fastening devices 488 mounted to the inner surface of the expandable portion 491 being moved inwardly toward the tether 436. Depending on the degree of inflation, the pins 488 can converge substantially such that they pierce through the tether 436 extending through the opening 492, transitioning the fixer assembly 485 from a first configuration of being disengaged with the tether 436 to a second configuration of being engaged with the tether 436. That is, the inflation of the expandable portion 491 results in the fixer assembly 485 engaging with the tether 436, securing the fixer assembly 485 and the epicardial pad (not shown) to the tether 436.

Figure 5B:
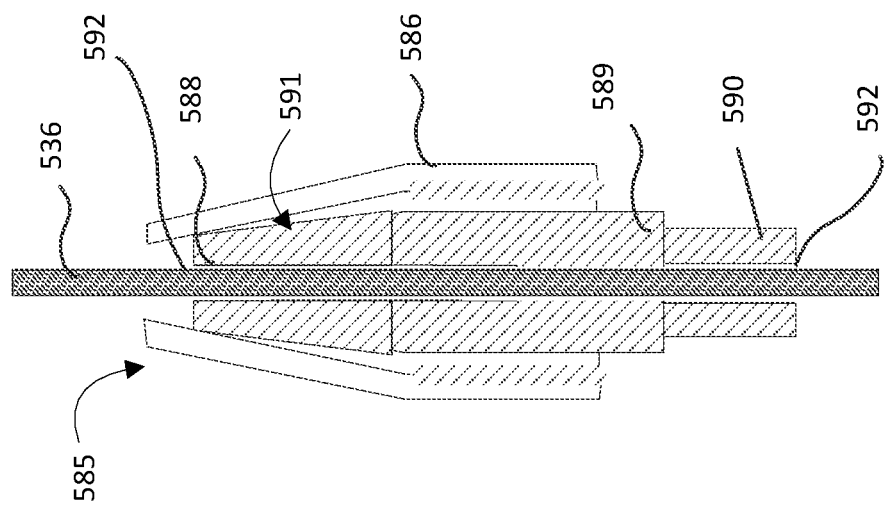
FIG. 5B is a cross-sectional view of the fixer assembly shown in FIG. 5A, taken along the line 5B-5B in FIG. 5A.
Figure 5A:
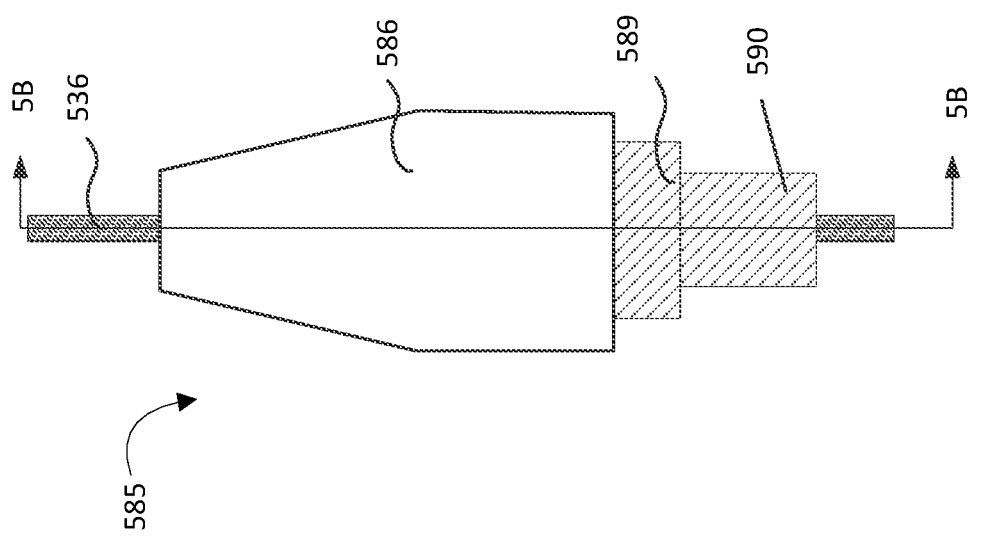
FIG. 5A is a schematic illustration of a fixer assembly, according to an embodiment.

In some embodiments, a fixer assembly can include a tether attachment device in the form of a pin vise or collet that upon rotary actuation clamps onto the tether extending through a central opening or shaft or lumen. One example of such an embodiment is illustrated in FIGS. 5A and 5B. FIG. 5A is an illustration of a side view of a fixer 585, and FIG. 5B is a cross-sectional view of the fixer 585. The fixer assembly 585 can be used in a similar manner as described above to secure an epicardial pad to a tether, and can be delivered and deployed following similar procedures as described with respect previous embodiments. For example, the fixer 585 has a bottom portion 590 to be placed against an epicardial pad or the apex of a heart (not shown in FIGS. 5A and 5B). In some instances, the bottom portion 590 of the fixer 585 can be configured to releasably engage with an epicardial pad through a suitable mechanism. For example, through screw threads in the bottom portion 590 that can matingly engage with tapped holes in the epicardial pad (not shown).

In this embodiment, the fixer 585 has a proximal actuation portion 586 that can be actuated by a delivery device, a movable portion 591, an intermediate portion 589, and a bottom or distal portion 590. The movable portion 591 can be actuated to engage and disengage with a tether, and the bottom or distal portion 590 can engage with an epicardial pad. The movable portion 591, the intermediate portion 589 and the bottom portion 590 collectively define a lumen 592 that can receive a tether 536 therethrough. The moveable portion 591 has an inner wall or surface 588 that can be clamped onto the tether 536 and function as a tether attachment portion, as described in more detail below. In some embodiments, as shown in FIGS. 5A and 5B, the movable portion 591 and the intermediate portion 589 can be formed integrally or monolithically as one component. In other embodiments, the movable portion 591 can be independent of the intermediate portion, as described for fixer 685 below, and illustrated in FIG. 6.

The actuation portion 586 can be actuated to transition the fixer 585 from a first configuration of not being engaged with a tether 536 to a second configuration of being engaged with a tether 536, as described below. The actuation portion 586 can be configured in any manner to effect movement of the movable portion 591 that results in the tether fastening portion 588 to clamp onto the tether 536. For example, the actuation of the fixer 585 can be similar to the function of a collet or a pin vise.

In some embodiments, the intermediate portion 589 can be attached to the bottom or distal portion 590. In some other embodiments, the intermediate portion 589 and the bottom portion 590 can be made integrally or monolithically as one piece. In some embodiments, the movable portion 591, the intermediate portion 589 and the bottom portion 590 can be made integrally to form one single piece. In the embodiments in which the intermediate portion 589 and the bottom portion 590 are not a single piece, they can each be adapted to have a suitable mechanism to releasably secure one against the other to minimize torque between the two portions during and after delivery and deployment. For example, the intermediate portion 589 and the bottom portion 590 can be adapted such that the intermediate portion 589 can be screwed onto or glued onto the bottom distal portion 590.

In some embodiments, the actuation portion 586 includes a suitable mechanism by which it can be engaged with the engagement portion of a delivery device (not shown) such that there is no relative torque or spinning movement between the delivery device and the actuation portion 586, or between the delivery device and the bottom portion 590 and the intermediate portion 589. For example, the intermediate portion 589 can have notches or grooves or other suitable features that can be engaged by corresponding features like pegs or protrusions or clamps in the delivery device.

The actuation portion 586 which, when actuated by a suitable mechanisms in the delivery device, can be configured to move the movable portion 591 such that the tether fastening portion 588 is made to engage with the tether 536. For example, the actuation portion 586 can be a screw cap 586 that can be tapped in its inner circumference to match a screw threaded on the outer circumference of intermediate portion 589 of the fixer 585. The actuation portion 586 can also have one or more adaptations such as a notch, groove or protrusion that can be matingly coupled to an actuation portion of the delivery device (not shown) such that it can be gripped by the delivery device and actuated by the delivery device.

In operation, during deployment, following the placement of a prosthetic heart valve within the native annulus of a heart, the tether 536 is attached to the prosthetic heart valve and extends out the apex of the heart. As described above, an epicardial pad and/or a fixer assembly 585 can be disposed within a delivery device and the tether 536 can be threaded through an opening in the epicardial pad and the lumen 592 in the fixer assembly 585. In some embodiments, the fixer assembly 585 can be coupled to the epicardial pad through a suitable coupling mechanism to assist during deployment.

A distal side of the epicardial pad can be disposed against the outside wall of the heart and the fixer assembly 585 can be moved to a position in contact with a proximal side of the epicardial pad. With the fixer assembly 585 in the desired position along the tether 536, the delivery device (not shown) can be actuated to engage with the actuation portion 586 to move the movable portion 591 into engagement with the tether 536. The actuation device can be used to rotate/turn (for example using suitable external control mechanisms in a handle of the delivery device) to apply torque to the actuation portion 586 such that the actuation portion 586 advances on the thread in the outer circumference of the intermediate portion 589. The progressive advancement of the actuation portion 586 progressively applies radial pressure on the outer diameter of the movable portion 591 and moves it radially inward towards the tether 536, constricting the lumen 592 at the top or distal portion (with respect to the heart) of the movable portion 591. The tether fastening portion 588 can apply a compressive force on the tether 536 to secure the fixer 585 to the tether 536. In some embodiments, in addition to or alternatively to the compressive force, the fastening portion 588 can include a pin(s) or other features that can engage the tether 536 to pierce or pin the tether 536. The engagement of the tether fastening portion 588 with the tether 536 fixes the relative position of the tether fixer assembly 585 on the tether 536, securing the epicardial pad to the tether 536.

Figure 6:
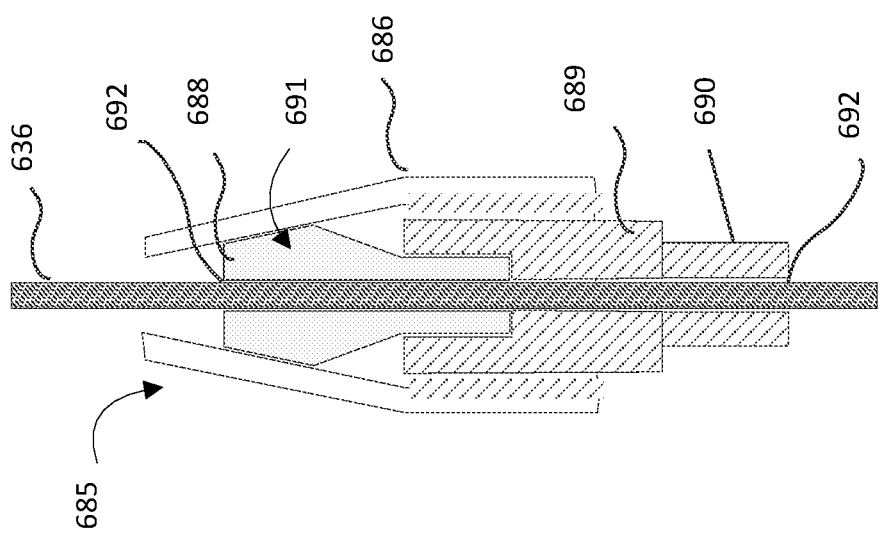
FIG. 6 is a cross-sectional view of a fixer assembly, according to another embodiment.

As described above, in some embodiments of a tether fixer assembly, the movable portion can be independent of the intermediate portion. One example of such an embodiment is shown in FIG. 6. The fixer assembly 685 can be similar or substantially the same as fixer assembly 585 and can be delivered and deployed to attach and secure a tether 636 to an epicardial pad in the same or similar manner as described above for tether fixer assembly 585. For example, the fixer assembly 685 can include a proximal actuation portion 686, a movable portion 691, an intermediate portion 689, and a bottom or distal portion 690. In this embodiment, the fixer assembly 685 includes a movable portion 691 that is a separate component from the intermediate portion 689 (i.e., not monolithically formed). A first portion of the inner surface of the actuation portion 686 includes a threaded portion that can be threadably coupled to a threaded portion on the outer diameter of the intermediate portion 689. A second portion of the inner surface of the actuation portion 686 can engage with an outer surface of the movable portion 691 over a length of the movable portion 691. The movable portion 691 also has an inner surface or tether attachment portion 688 that is configured to engage a tether 636 in a similar manner as described for fixer 585. A lumen 692 is defined collectively by the moveable portion 691, the intermediate portion 689 and the distal portion 690 through which a tether 636 can be received.

The second portion of the inner surface of the actuation portion 686 can have a diameter that tapers to a size that is slightly smaller than an outer surface of the movable portion 691. Thus, advancement of the actuation portion 686 in the direction of the intermediate portion 689 results in a radial compression of the movable portion 691, and the tether attachment portion 688 engages the tether 636, securing the tether 636 to the fixer 685 with a clamping force. More specifically, as described above, the progressive advancement of the actuation portion 686 on the threaded portion of the intermediate portion 689 can progressively apply a radial force on the outer surface of the movable portion 691, which moves the movable portion 691 radially inward towards the tether 636. The radial force effected in the movable portion 691 results in constricting the lumen 692 along the length of the movable portion 691. The tether fastening portion 688, can apply a compressive force to retain the tether 636 and/or can include a pin or pins or other like adaptations disposed on the inner surface of the movable portion 691 such that inward movement of the movable portion 691 results in pinning and/or clamping of the tether 636.

Following deployment, the delivery device can be uncoupled from the tether fixer assembly 585, 685 through any suitable means and the delivery device can be retracted out of the patient's body through the minimally invasive opening used for the delivery. For example, the engagement with the tether fixer assembly 585, 685 can be through clamps or pegs on the engagement and actuation portions of the delivery device that are matingly connected to grooves or notches on the tether fixer assembly 585, 685 and held in place by radial compression via a delivery sheath. Following deployment, the delivery sheath holding the engagement can be retracted to release the engagement thereby uncoupling the delivery device from the tether fixer assembly. The delivery device can then be retracted out of the patient's body.

Figure 8:
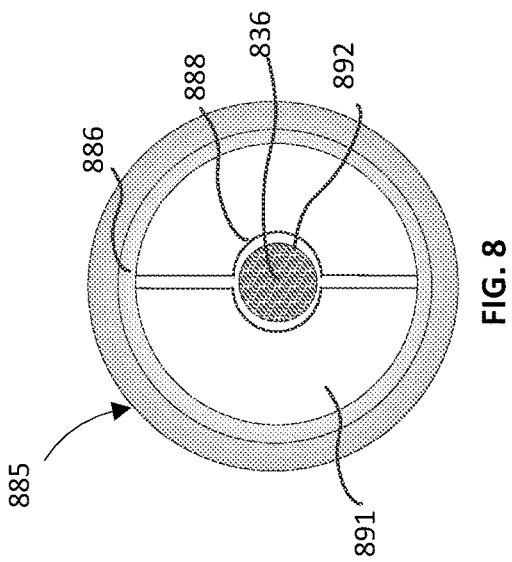
FIGS. 7, 8, and 9 are each a schematic illustration of top views of fixer assemblies, according to three different embodiments.
Figure 7:
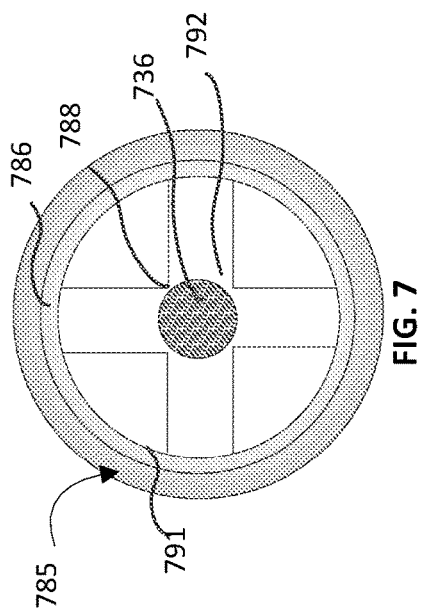
Figure 9:
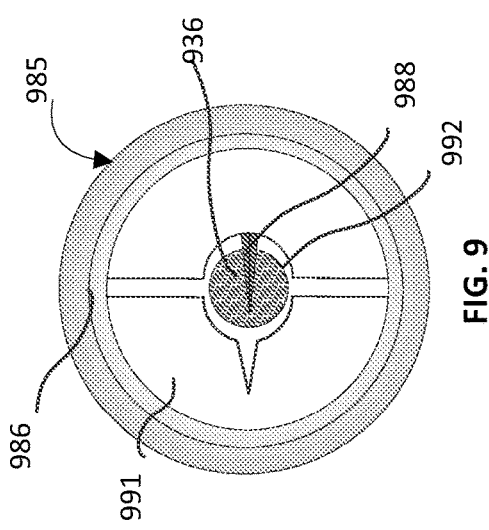

FIGS. 7, 8 and 9 show top views of three different embodiments of a tether fixer assembly 785, 885 and 985, respectively, that can be similar to the tether fixer assemblies 585 and 685 in that they can be a vise type configuration. Each tether fixer assembly has an actuation portion 786, 886 and 986, and a movable portion 791, 891, and 991 with corresponding tether attachment portions 788, 888, and 988, respectively. The tether attachment portions 788 of fixer assembly 785 are shaped in the form of four pincer like members in four quadrants of the movable portions 791. FIG. 7 illustrates the position of the tether attachment portions 788 before engaging with the tether 736. Upon actuation of the fixer assembly 785, the attachment portions 788 are configured to be moved radially inward and pin the tether 736 at four locations upon radial compression of the movable portion 791 due to the advancement of the actuation portion 786 in a similar manner as described above for tether fixers 585 and 685.

The tether attachment portions 888 of tether fixer 885 are shaped in the form of semi-circular clamps on the inner surface of the movable portion 891. Upon actuation of the tether fixer 885, the attachment portions 888 move inward and apply a clamping force on the tether 836. FIG. 8 illustrates the fixer assembly 885 before actuation, when the tether attachment portions 888 are not engaged with the tether 836. When the tether fixer 885 is actuated, the advancement of the actuation portion 886 results in the radial compression of the movable portion 891. This in turn moves the two semi-circular halves of the movable portion 891 inward, resulting in the attachment portions 888 piercing the tether 836 to fix the relative position of the tether fixer 885 on the tether 836.

With the tether fixer 985, the tether attachment portion 988 is in the form of a pin disposed on an inner surface of the movable portion 991, which may also be shaped as two semi-circular halves. The inner diameter of the movable portion 991 can be smaller, larger or the same as the tether 936. The advancement of the actuation portion 986 radially compresses the movable portion 991 bringing the two semi-circular halves closer together, resulting in the attachment portion 988 piercing the tether 936. FIG. 9 illustrates the position of the attachment portion 988 when engaged with the tether 936 upon actuation through advancement of the actuation portion 986.

In some other embodiments, the tether fixer assemblies described herein can include a rotary actuator coupled to a cam-pin device such that a semi-circular or partially circular pin or needle is advanced along a circular track through an opening through which the tether extends through the tether fixer assembly. One such example embodiment is illustrated in FIGS. 10A-10E.

Figure 10A:
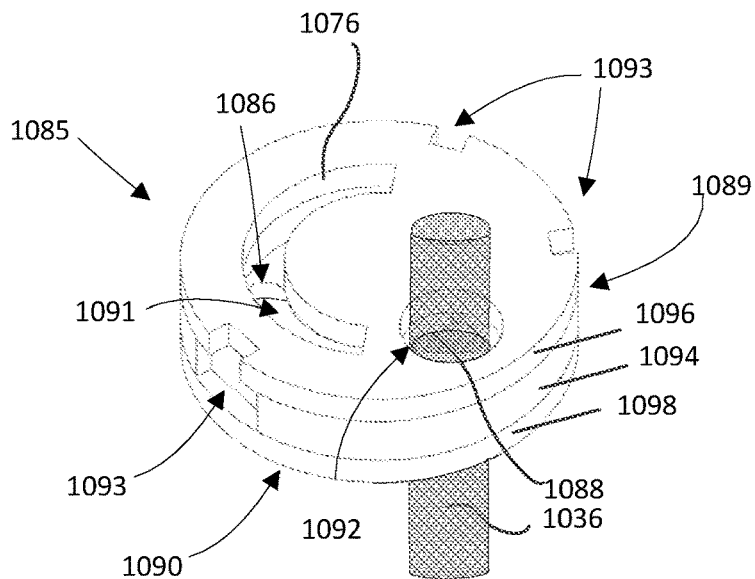
FIGS. 10A and 10B are illustrations of side perspective views of a fixer assembly according to an embodiment.
Figure 10B:
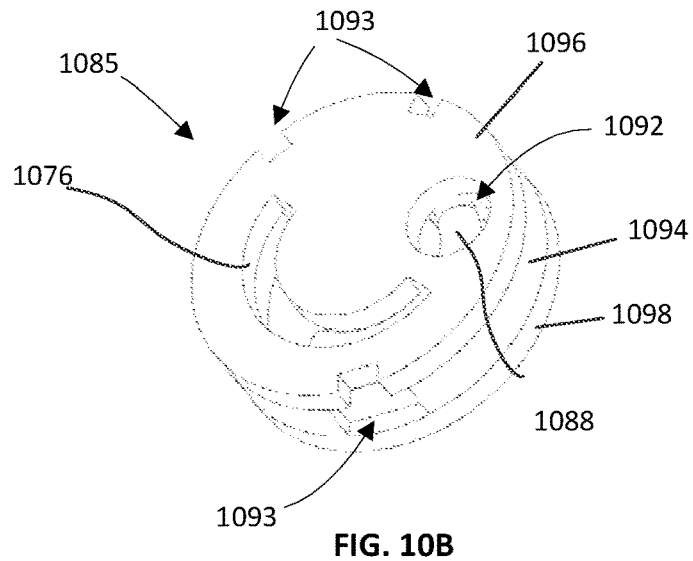
Figure 10C:
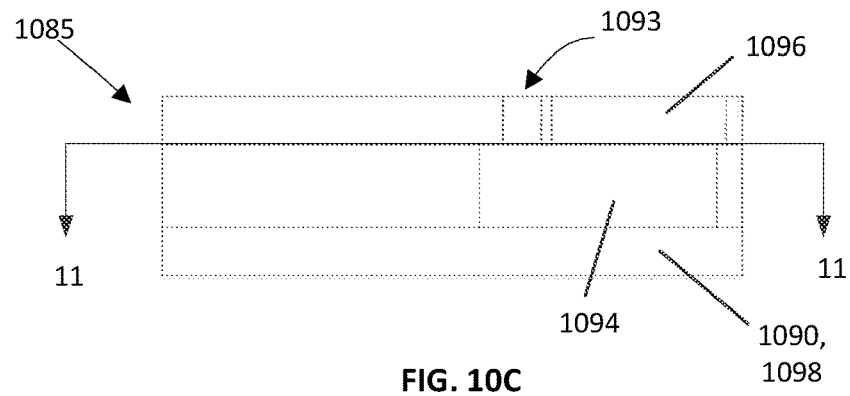
FIG. 10C is an illustration of a side view of the fixer assembly of FIGS. 7A and 7B.

FIGS. 10A and 10B show two perspective views of a tether fixer assembly 1085, with FIG. 10A illustrating a portion of a tether 1036. FIG. 10C illustrates a side view and FIGS. 10 D and 10E show a top view and bottom view of the tether fixer assembly 1085, with the tether 1036. The fixer assembly 1085 can be similar to or substantially the same as the tether fixer assemblies 185 and 285 described above and can be used in a similar manner as described above to secure an epicardial pad to a tether. The fixer assembly 1085 can be delivered and/or deployed following procedures similar to or substantially the same as those described with respect to previous embodiments.

Figure 10E:
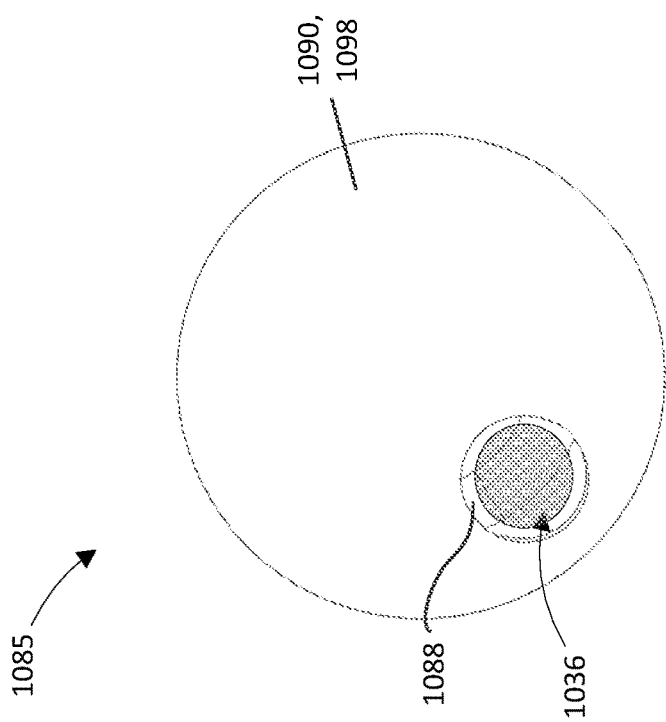
FIGS. 10D and 10E are illustrations of a top and bottom view of the fixer assembly of FIGS. 10A and 10B, respectively.
Figure 10D:
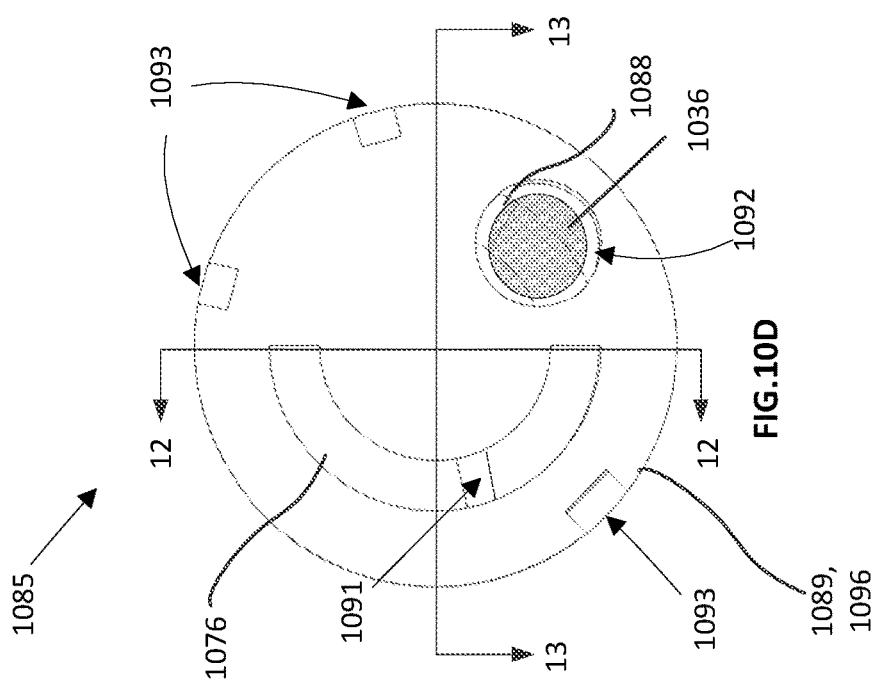

In this embodiment, the fixer 1085 has a proximal engagement portion 1089 and a distal portion 1090. In some embodiments, the proximal engagement portion 1089 includes a top plate 1096 and an intermediate plate 1094. The distal portion 1090 can include a bottom plate 1098 that can be placed against an epicardial pad. The top plate 1096, the intermediate plate 1094 and the bottom plate 1098 are secured against relative rotational movement about their central axes. The top plate 1096, the intermediate plate 1094, and the bottom plate 1098 can be made separately and joined together in some embodiments, or in other embodiments, they can be made integrally or monolithically as one piece. The fixer assembly 1085 includes a lumen 1092 collectively defined by the top plate 1096, the intermediate plate 1094 and the bottom plate 1098 through which a tether 1036 coupled to a prosthetic heart valve can be received. FIGS. 10A, 10D and 10E show portions of the tether 1036.

The top plate 1096 and the intermediate plate 1094 can engage with an engagement portion of a delivery device (not shown). For example, the top plate 1096 and the intermediate plate 1094 each define notches 1093 that can couple with matching components such as pegs or pins of the delivery device, to maintain the rotational position of the tether fixer assembly 1085, with respect to the delivery device during delivery and deployment. As shown, for example, in FIGS. 10A and 10B, the notches 1093 of the top plate 1096 and the notches of the intermediate plate 1094 substantially align with each other, and the notches 1093 of the intermediate plate 1094 have a larger width than the notches 1093 of the top plate 1096.

Figure 11A:
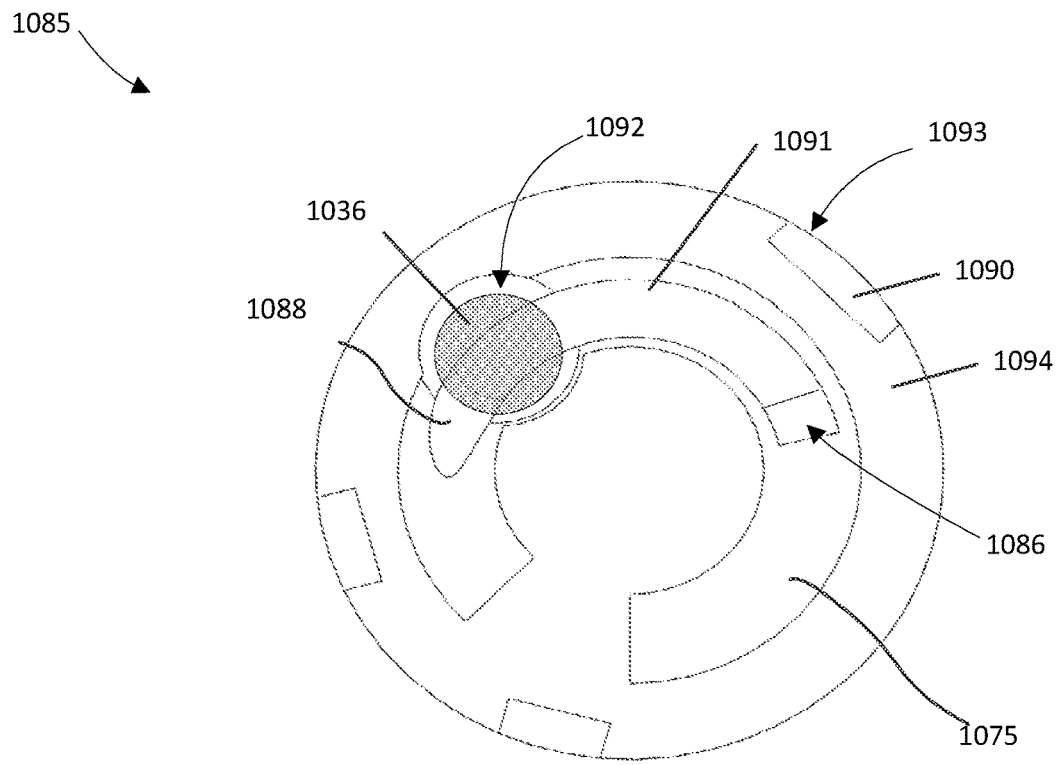
FIG. 11A is an illustration of a top view of a cross-section of the fixer assembly shown in FIG. 10C, taken along the line 11-11, with the top layer removed.
Figure 11B:
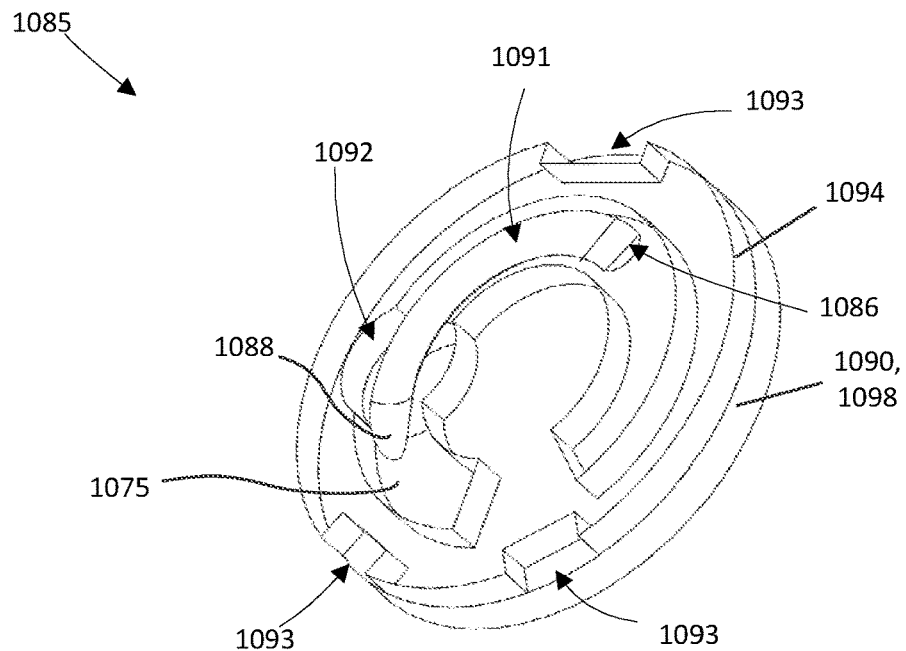
FIG. 11B is an illustration of a perspective view of the cross-section of the fixer assembly shown in FIG. 10C, taken along the line 11-11.

The fixer assembly 1085 also includes a movable portion 1091 that can move along a curved track 1075 defined by the intermediate plate 1094 (see e.g., FIGS. 11A and 11B). The movable portion 1091 is curve shaped and includes a tether piercing tip portion 1088. The top plate 1096 defines a curved slot 1076 that is in fluid communication with the curved track 1075, and the curved track 1075 is in fluid communication with the lumen 1092. The fixer assembly 1085 can be moved between a first configuration in which the tip portion 1088 is not engaged with the tether, and a second configuration in which the tip portion 1088 is engaged with the tether (e.g., the tip portion 1088 pierces the tether 1036). For example, upon actuation of the fixer assembly 1085, the movable portion 1091 can travel or move along the curved track 1075 and the tip portion 1088 can pierce through the tether 1036 extending through the lumen 1092. FIGS. 10A, 10B and 10D and 10E illustrate the movable portion 1091 in an actuated position (i.e., the fixer assembly 1085 is in the second configuration) with the tip portion 1088 shown passed through the lumen 1092. FIGS. 10A, 10D and 10E show a portion of the tether 1036 with partial transparency to show the tip portion 1088 pierced through the tether 1036.

FIG. 11A illustrates a top view of a cross-section of the tether fixer assembly 1085 taken along the line 11-11 indicated in 10C, and FIG. 11B illustrates a perspective view of the same cross-section of the tether fixer 1085. As shown in FIGS. 11A and 11B, the fixer assembly 1085 is in the second configuration with the tether piercing portion 1088 of movable portion 1091 engaged with and piercing the tether 1036, shown partially transparent in FIG. 11A.

Figure 12A:
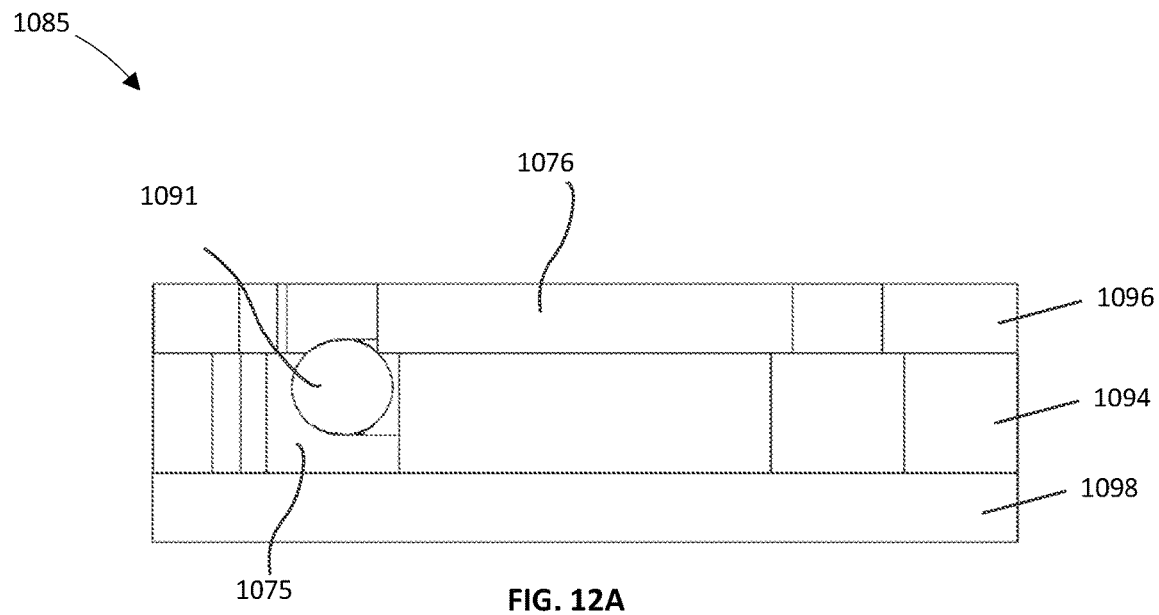
FIG. 12A is an illustration of a side view of a cross-section of the fixer assembly shown in FIG. 10D, taken along the line 12-12.
Figure 12B:
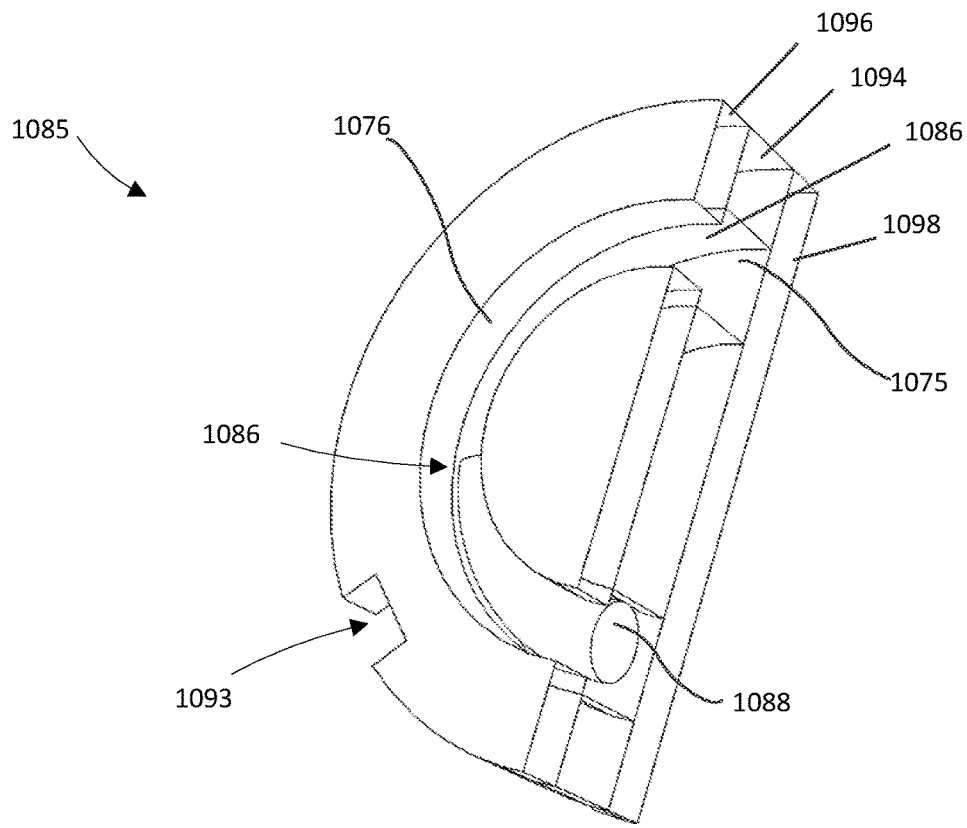
FIG. 12B is an illustration of a perspective view of the cross-section of the fixer assembly shown in FIG. 10D, taken along the line 12-12.
Figure 13A:
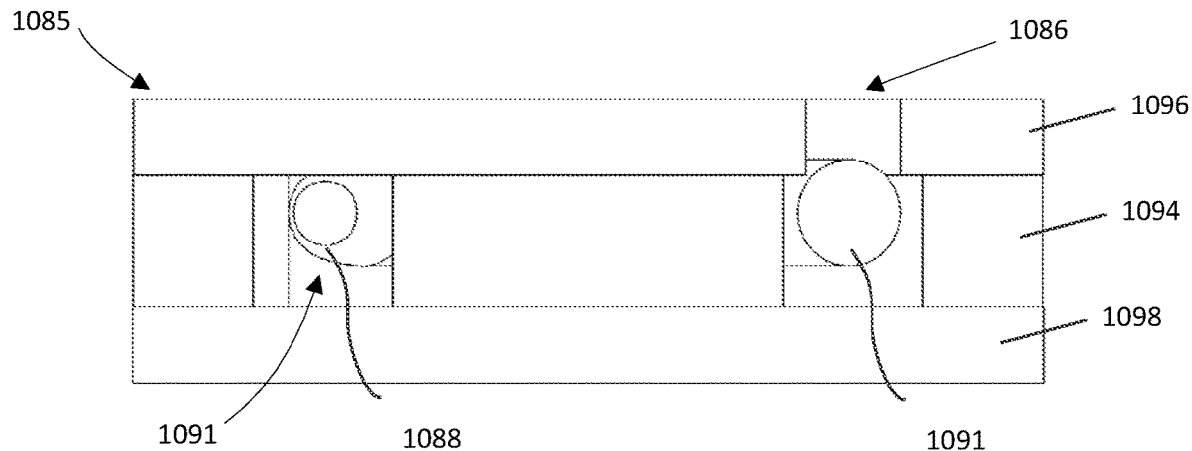
FIG. 13A is an illustration of a side view of a cross-section of the fixer assembly shown in FIG. 10D, taken along the line 13-13.
Figure 13B:
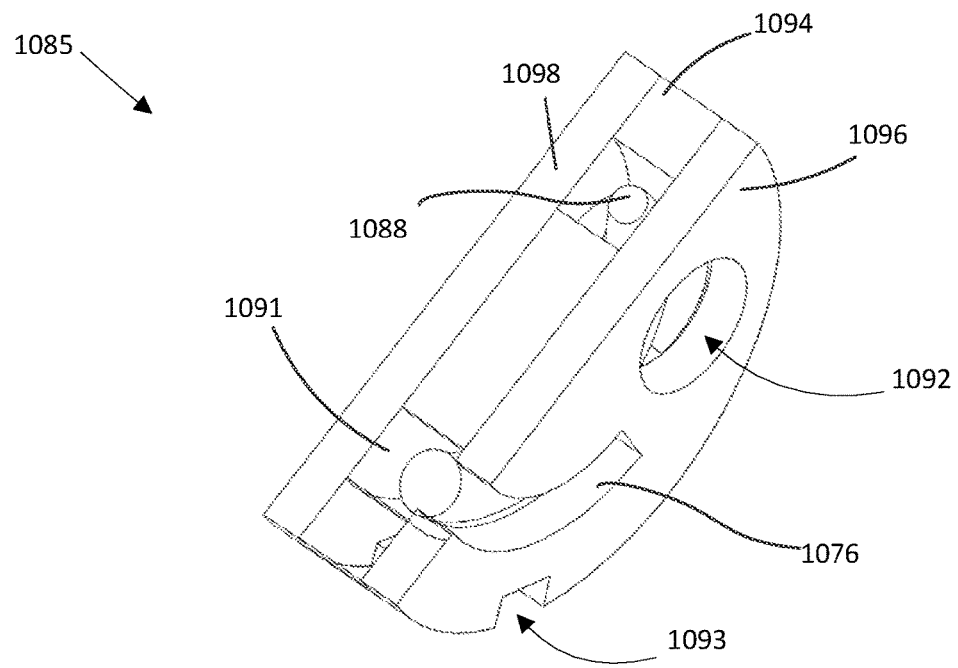
FIG. 13B is an illustration of a perspective view of the cross-section of the fixer assembly shown in FIG. 10D, taken along the line 13-13.

FIGS. 12A and 12B illustrate a side view and a perspective view of a cross section of the fixer assembly 1085 taken along line 12-12 in FIG. 10D. Only the left half of the fixer assembly 1085 is illustrated in FIGS. 12A and 12B, to show the circular track 1075 and the moveable portion 1091. 13A and 13B illustrate a side view and a perspective view of a cross-section of the fixer 1085 taken along the line 13-13 in FIG. 10D. Only the bottom half of the fixer assembly 1085 is illustrated in FIGS. 13A and 13B. The movable portion 1091 can be seen at both ends of the circular track 1075.

In operation, the fixer assembly 1085 can be delivered using a delivery device, as described above with respect to fixer assemblies 185 or 285, or fixer assemblies 385, 485, and/or 585. For example, following the deployment of a prosthetic heart valve in the native annulus of a heart, the tether fixer 1085 can be used to secure a tether 1036 extending from the prosthetic heart valve to an epicardial pad to secure the position of the prosthetic valve within the heart. The epicardial pad and the fixer assembly 1085 can be delivered through a minimally invasive opening in the patient as described above for previous embodiments. The tether 1036 can be threaded or received through an opening in the epicardial pad and the lumen 1092 of the fixer assembly 1085 and the epicardial pad and the fixer assembly can be placed within a lumen of the delivery device and deployed, simultaneously or sequentially, as described in more detail below. The delivery device can include one or more control mechanisms, within, for example, a handle of the delivery device that can be used to actuate the fixer assembly 1085 to move the fixer assembly 1085 between its first configuration and second configuration.

As described above, the notches 1093 can be matingly and removably coupled to corresponding features of a delivery device such as pegs or pins, to maintain the rotational position of the tether fixer assembly 1085 with respect to the delivery device during delivery and deployment. For example, the corresponding engagement features of the delivery device can be t-shaped and be received within t-shaped notches formed by the notches 1093 of the top plate 1096 and the notches 1093 of the intermediate plate 1094. With the t-shaped engagement features of the delivery device disposed within the notches 1093, a sheath of the delivery device can be placed over the fixer assembly 1085 such that the inner walls of the sheath hold and maintain the t-shaped engagement features within the t-shaped notches 1093. Thus, during delivery, the sheath prevents the t-shaped engagement features from coming out of the notches 1093 in a lateral or radial direction. As described above, the tight connection between the engagement features of the delivery device and the notches 1093 prevents rotational movement of the tether fixer assembly 1085 relative to the delivery device during delivery.

The delivery device can also include a driver or actuation member that can engage with and actuate the movable portion 1091. For example, the driver member can engage with an actuation portion 1086 of the movable portion 1091. Upon positioning the tether fixer 1085 at a desired position along the tether 1036 and against a proximal side of the epicardial pad, the actuation member of the delivery device can be used to actuate the fixer 1085. Actuation of the fixer 1085 causes the movable portion 1091 to move within the curved track 1075 until the tether piercing tip portion 1088 engages and pierces the tether 1036 extending through the lumen 1092. The fixer assembly 1085 can also include a lock mechanism (not shown) that secures the fixer assembly 1085 in the second configuration after actuation and piercing of the tether. For example, a lock feature can be disposed within the track 1075 that when the movable portion 1091 has traveled a preselected distance within the track 1075, the movable portion 1091 engages with the lock and is prevented from moving backwards within the track 1075. In some embodiments, the tether fixer assembly 1085 can be secured in the second configuration, due to frictional forces between the tip portion 1088 and the tether 1036. In some other embodiments, the lock mechanism of the fixer assembly 1085 can include one or more clasping or clamping mechanisms (not shown) disposed along the circular track 1075 that allow forward movement of the movable portion 1091 and prevent any backward movement of the movable portion 1091. For example, the fixer assembly 1085 can include one or more clamps or seals that are in an open state during deployment and actuation allowing forward movement of the movable portion 1091. When the tip portion 1088 has sufficiently pierced through the tether 1036 or upon the movable portion 1091 engaging the clamps or seals, the clamps or seals can be actuated actively or passively to transition into a closed state to prevent any backward movement of the movable portion 1091.

After the epicardial pad and the fixer assembly 1085 have been positioned against the apex of the heart and secured to the tether 1036, the delivery device can be uncoupled from the tether fixer assembly 1085 by disengaging the engagement portion of the delivery device from the engagement notches 1093 of the fixer assembly 1085. For example, in some embodiments, where the engagement is held through radial forces applied by the sheath of the delivery device, the sheath can be retracted proximally allowing the engagement features of the delivery device to be released from the notches 1093. Upon the release of the engagement features, the delivery device can be retracted and removed from the patient's body.

Figure 14A:
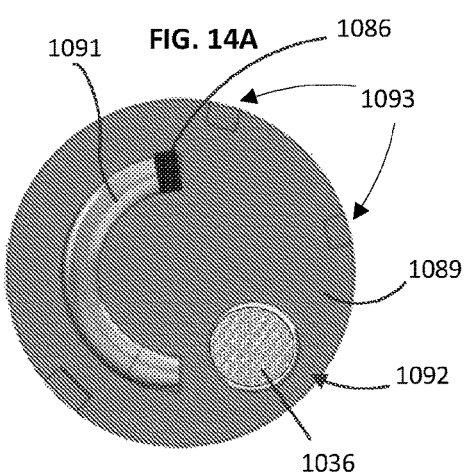
FIGS. 14A-14D are each a top view of the fixer assembly of FIGS. 10A-10E, and FIGS. 11A, 11B, 12A, 12B, 13A, 13B, illustrating the transition of the fixer assembly between a first configuration and a second configuration.

FIGS. 14A-14D illustrate the transition of the fixer assembly 1085 from the first configuration to the second configuration. FIG. 14A illustrates the fixer assembly 1085 in the first configuration when it is not engaged with the tether 1036, which is shown as a partially transparent patterned circle within the opening 1092. For example, FIG. 14A shows the tip portion 1088 when it is not engaged with the tether 1036.

Figure 14B:
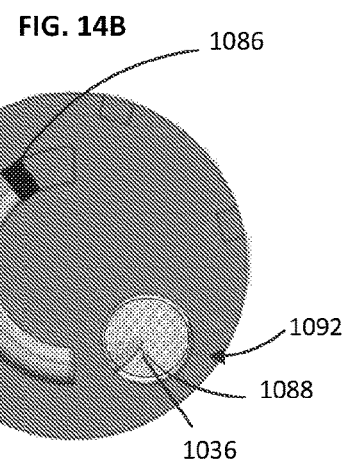
Figure 14C:
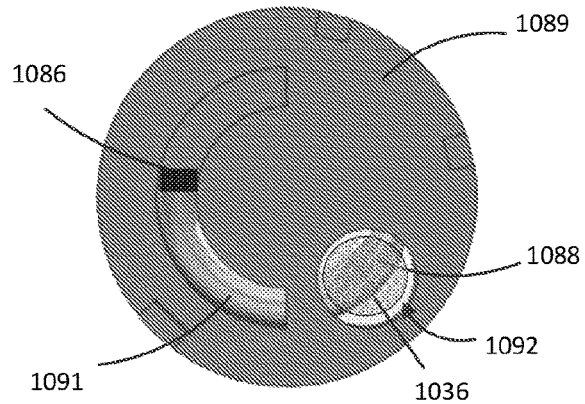
Figure 14D:
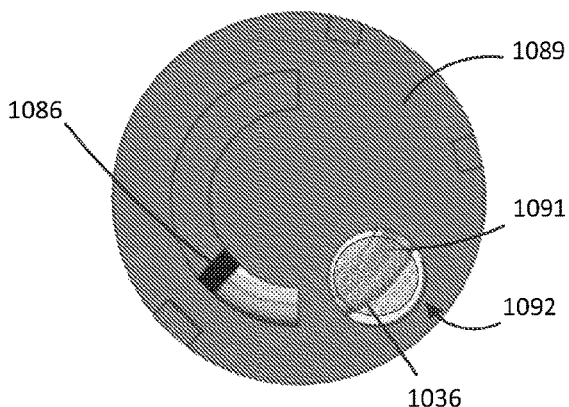
Figure 15:
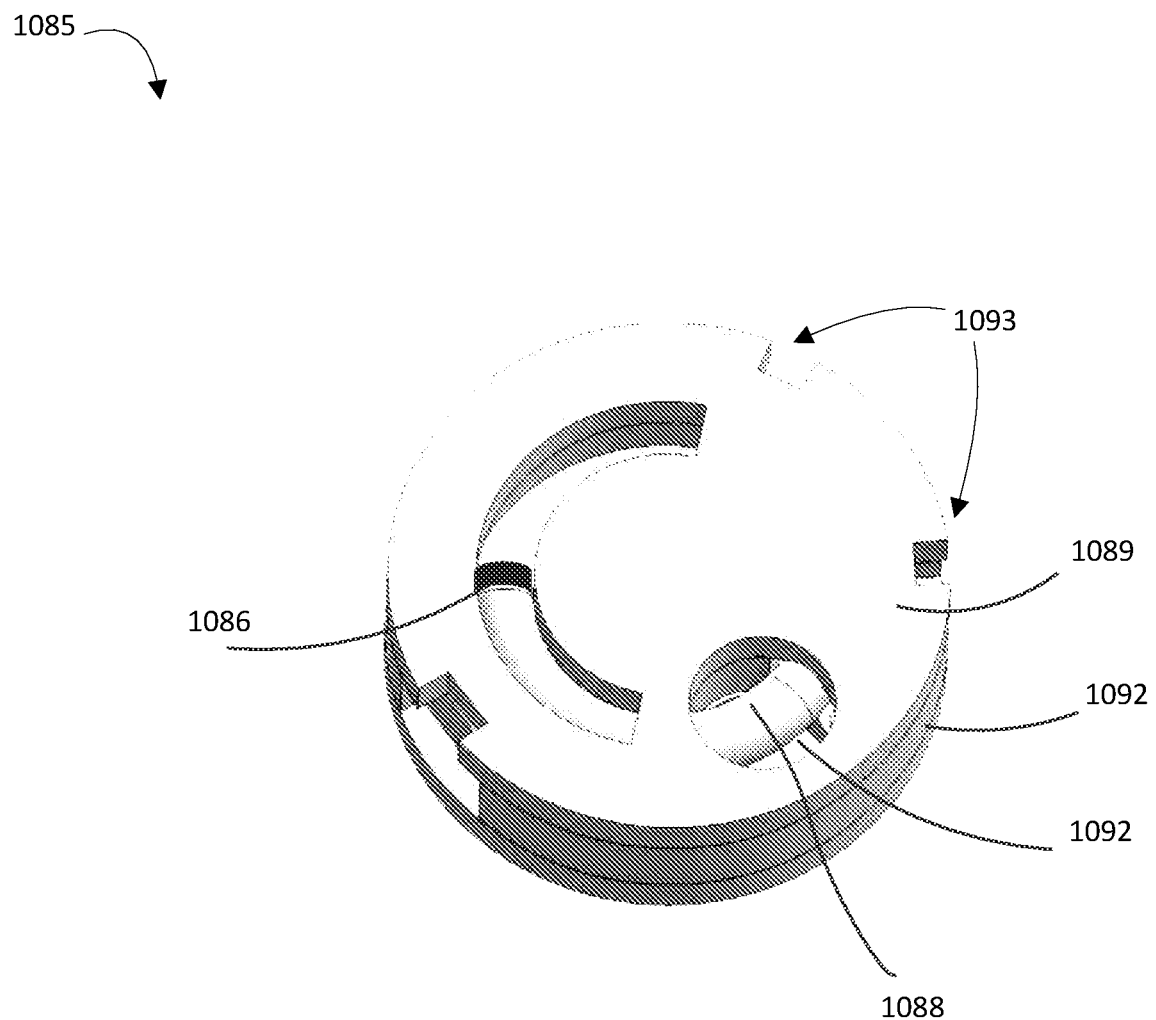
FIG. 15 is a perspective view of the fixer assembly shown in FIGS. 14A—14D, showing the pin in an extended position.

As the delivery device actuates the fixer assembly 1085, the movable portion 1091 will be caused to travel through the curved track 1075 resulting in the progressive insertion of the tip portion 1088 into the tether 1036 as shown in FIG. 14B. FIGS. 14B, 14C and 14D show the progression of the tip portion 1088 as it pierces through the tether 1036 and the fixer 1085 is moved to its second configuration.

Although not shown for all embodiments, any of the embodiments of a delivery device or system can include a handle or handle assembly to which the various delivery sheaths, engagement portions, and actuation portions of the delivery device can be operatively coupled and which a user (e.g., physician) can grasp and use to manipulate the delivery device or its components. For example, the handle assembly can include controls to move the various delivery sheaths and other components, as described in the '077 publication incorporated by reference above.

In addition, the systems and methods described herein can also be adapted for use with a prosthetic tricuspid valve. For example, in such a case, a procedural catheter can be inserted into the right ventricle of the heart, and the delivery sheath delivered to the right atrium of the heart either directly (transatrial), or via the jugular or femoral vein. In such a case, the delivery devices to deliver an epicardial pad can be disposed outside the heart below the right ventricle and/or be inserted within the right ventricle depending on the particular embodiment of the epicardial pad being delivered.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. A system, comprising:
   a prosthetic heart valve having a tether extending therefrom and outside a heart when the prosthetic heart valve is disposed within the heart;
   an epicardial pad configured to be disposed outside of the heart to secure the prosthetic heart valve in a desired position within the heart, the epicardial pad defining an opening through which the tether is configured to extend; and
   a fixer assembly configured to be coupled to the epicardial pad, the fixer assembly defining a lumen configured to receive a portion of the tether extending from the epicardial pad therethrough, the fixer assembly including a movable portion and being movable between a first configuration in which the moveable portion is disengaged with the tether, and a second configuration in which the movable portion is engaged with the tether, the fixer assembly configured to secure the epicardial pad to the tether to secure the prosthetic heart valve in the desired position within the heart,
   wherein the fixer assembly includes a first end, a second end, an elongate member extending from the first end to the second end and defining the lumen, and at least one actuation member extending between the first end and the second end, the actuation member configured to move the fixer assembly between the first configuration and the second configuration upon actuation,
   wherein the actuation member is a screw.

2. A system, comprising:
   a prosthetic heart valve having a tether extending therefrom and outside a heart when the prosthetic heart valve is disposed within the heart;
   an epicardial pad configured to be disposed outside of the heart to secure the prosthetic heart valve in a desired position within the heart, the epicardial pad defining an opening through which the tether is configured to extend; and
   a fixer assembly configured to be coupled to the epicardial pad, the fixer assembly defining a lumen configured to receive a portion of the tether extending from the epicardial pad therethrough, the fixer assembly including a movable portion and being movable between a first configuration in which the moveable portion is disengaged with the tether, and a second configuration in which the movable portion is engaged with the tether, the fixer assembly configured to secure the epicardial pad to the tether to secure the prosthetic heart valve in the desired position within the heart, wherein the fixer assembly is expandable and has an inflated condition and a deflated condition, wherein upon transition from the deflated condition to the inflated condition, an outer diameter of the fixer assembly remains fixed and an inner diameter of the fixer assembly decreases, the inner diameter at least partially defining the lumen.

3. The system of claim 2, wherein the fixer assembly include at least one fastening device positioned on an interior surface of the fixer assembly, the fastening device including a tip oriented toward the lumen.

4. The system of claim 3, wherein the tip of the fastening device engages the tether when the fixer assembly is in the inflated condition.

5. A system, comprising:
a prosthetic heart valve having a tether extending therefrom and outside a heart when the prosthetic heart valve is disposed within the heart;
an epicardial pad configured to be disposed outside of the heart to secure the prosthetic heart valve in a desired position within the heart, the epicardial pad defining an opening through which the tether is configured to extend; and
a fixer assembly configured to be coupled to the epicardial pad, the fixer assembly defining a lumen configured to receive a portion of the tether extending from the epicardial pad therethrough, the fixer assembly including a movable portion and being movable between a first configuration in which the moveable portion is disengaged with the tether, and a second configuration in which the movable portion is engaged with the tether, the fixer assembly configured to secure the epicardial pad to the tether to secure the prosthetic heart valve in the desired position within the heart,
wherein the fixer assembly includes a proximal engagement portion having a top plate and an intermediate plate, and a distal portion having a bottom plate,
wherein the intermediate plate defines a curved track, a curved movable portion having a piercing tip and being movably received within the curved track.

6. The system of claim 5, wherein in the first configuration of the fixer assembly, the curved movable portion does not traverse the lumen, and in the second configuration of the fixer assembly, the curved movable portion does traverse the lumen.

7. The system of claim 6, further comprising:
a delivery device having a sheath, an actuation device configured to transition the fixer assembly from the first condition to the second condition, and an engagement portion for releasably engaging the fixer assembly.

8. The system of claim 7, wherein at least one of the top plate and the intermediate plate define notches that are configured to mate with the engagement portion of the delivery device to maintain a rotational position of the fixer assembly while the notches are mated with the engagement portion of the delivery device.

9. The system of claim 7, wherein the actuation device is configured to drive the curved movable portion along the curved track.

10. The system of claim 7, wherein the fixer assembly includes a lock mechanism that allows the curved movable portion to move along the curved track in a first direction, but prevents the curved movable portion from moving along the curved track in a second direction opposite the first direction.

\* \* \* \* \*